United States Patent [19]

Ogura et al.

[11] Patent Number: 4,874,861
[45] Date of Patent: Oct. 17, 1989

[54] PYRIDAZINONE DERIVATIVES, PREPARATION THEREOF, AND INSECTICIDAL, ACARICIDAL, NEMATICIDAL, FUNGICIDAL COMPOSITIONS

[75] Inventors: Tomoyuki Ogura; Yasuo Kawamura; Shigeru Ishii; Masatoshi Baba; Masakazu Taniguchi, all of Funabashi; Masayoshi Hirose, Shiraoka; Kiminori Hirata, Shiraoka; Yoshinori Ochiai, Shiraoka, all of Japan

[73] Assignee: Nissan Chemical Industries, Ltd., Tokyo, Japan

[21] Appl. No.: 127,518

[22] Filed: Nov. 30, 1987

Related U.S. Application Data

[63] Continuation of Ser. No. 800,665, Nov. 22, 1985, abandoned.

[30] Foreign Application Priority Data

Nov. 29, 1984 [JP] Japan .................. 59-252123
May 22, 1985 [JP] Japan .................. 60-109624

[51] Int. Cl.$^4$ .................. C07D 237/18; C07D 237/16; C07D 403/12; C07D 401/12
[52] U.S. Cl. .................. 544/229; 544/238; 544/240
[58] Field of Search .................. 544/229, 238, 240; 514/247, 252, 253

[56] References Cited

U.S. PATENT DOCUMENTS

| | | | |
|---|---|---|---|
| 2,832,780 | 4/1958 | King | 540/239 |
| 3,137,696 | 6/1964 | Reicheneder | 544/240 |
| 3,346,577 | 10/1967 | Nakagome et al. | 544/239 |
| 4,177,273 | 12/1979 | Bennett | 544/239 |
| 4,571,397 | 2/1986 | Taniguchi | 571/92 |
| 4,576,630 | 3/1986 | Parg et al. | 544/239 |
| 4,663,324 | 5/1987 | Graf et al. | 544/240 |
| 4,783,462 | 11/1988 | Matsukado | 544/238 |

FOREIGN PATENT DOCUMENTS

| | | |
|---|---|---|
| 1192195 | 8/1983 | Canada . |
| 78450 | 5/1983 | European Pat. Off. . |
| 88384 | 9/1983 | European Pat. Off. . |

(List continued on next page.)

OTHER PUBLICATIONS

Taniguchi, Chem Abs 100, 34565m (1983).
Patent Abstracts of Japan, Abstract of JP-6054319.
Patent Abstracts of Japan, Abstract of JP-6004173.
Japanese Patent Abstract of Laid-Open Appln JP 60-4173, May 16, 1985, vol. 9, No. 112.
Japanese Patent Abstract of Laid-Open Appln JP 60-54319, Jul. 30, 1985, vol. 9, No. 184.
Gymen, Chemical Abstract No. 114552g, vol. 93, 1980.
Wilson, Chemical Abstract No. 20533h, vol. 91, 1979.
Begila, Chemical Abstract No. 124615j, vol. 78, 1972.
Kaji, Chemical Abstract No. 106726f, vol. 69, 1968.
Taniguchi, Chemical Abstract No. 34565m, vol. 100, 1984.
Kaji, Chemical Abstract No. 30484u, vol. 71, 1969.
Kaji, Chemical Abstract No. 10672h, vol. 69, 1968.
Kaju, Chem. Abs., vol. 70, 1969, 28883j, Synthesis of Sulfur-Containing Pyridazines.

Primary Examiner—Mark L. Berch
Attorney, Agent, or Firm—Oliff & Berridge

[57] ABSTRACT

Novel 3(2H)-pyridazinone derivatives having the general formula (I):

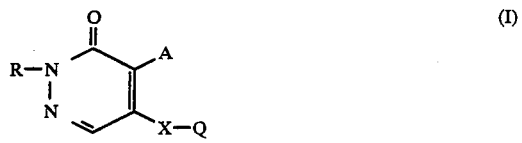

wherein, R denotes a straight or branched $C_1$ to $C_6$ alkyl; A denotes a straight or branched $C_1$ to $C_6$ alkyl or a halogen; X denotes oxygen or sulfur atom; Q denotes a group;

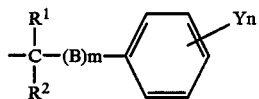

when A is a straight or branched $C_1$ to $C_6$ alkyl, and Q denotes a group:

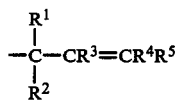

when A is a halogen atom; $R^1$ and $R^2$ denote each independently hydrogen, a lower alkyl, a lower haloalkyl, or 4-tert-butylphenyl; B denotes —$CR^6$=$CR^7$—, —$CR^6R^7O$—, or

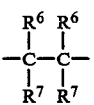

(wherein, $R^6$ and $R^7$ denote various specific organic radicals. A process for preparation of said derivatives is also provided. These derivatives are useful as an active ingredient of insecticidal, acaricidal, nematicidal and/or fungicidal compositions for agricultural and horticultural uses as well as of expellent compositions for ticks parasitic on animals.

3 Claims, No Drawings

FOREIGN PATENT DOCUMENTS

| | | |
|---|---|---|
| 134439 | 3/1985 | European Pat. Off. . |
| 135076 | 3/1985 | European Pat. Off. . |
| 183212 | 6/1986 | European Pat. Off. . |
| 193853 | 9/1986 | European Pat. Off. . |
| 199281 | 10/1986 | European Pat. Off. . |
| 232825 | 8/1987 | European Pat. Off. ............ 544/240 |
| 3143303 | 5/1983 | Fed. Rep. of Germany . |
| 3328770 | 2/1985 | Fed. Rep. of Germany . |
| 2250397 | 7/1985 | Fed. Rep. of Germany . |
| 41-2459 | 2/1966 | Japan . |
| 41-2788 | 2/1966 | Japan . |
| 42-1302 | 1/1967 | Japan . |
| 42-9344 | 5/1967 | Japan .................................. 544/240 |
| 429344 | 5/1967 | Japan . |
| 43-11902 | 5/1968 | Japan . |
| 43-11903 | 5/1968 | Japan . |
| 43-11904 | 5/1968 | Japan . |
| 43-11905 | 5/1968 | Japan . |
| 43-11907 | 5/1968 | Japan . |
| 43-11908 | 5/1968 | Japan . |
| 43-11909 | 5/1968 | Japan . |
| 43-119065 | 5/1968 | Japan . |
| 44-8857 | 4/1969 | Japan . |
| 44-8858 | 4/1969 | Japan . |
| 44-8860 | 4/1969 | Japan . |
| 44-88594 | 4/1969 | Japan . |
| 44-88614 | 4/1969 | Japan . |
| 44-12421 | 6/1969 | Japan . |
| 61-130275 | 6/1986 | Japan . |
| 61-243078 | 10/1986 | Japan . |
| 61-268672 | 11/1986 | Japan . |
| 62-016470 | 1/1987 | Japan .................................. 544/240 |

PYRIDAZINONE DERIVATIVES, PREPARATION THEREOF, AND INSECTICIDAL, ACARICIDAL, NEMATICIDAL, FUNGICIDAL COMPOSITIONS

This application is a continuation of Ser. No. 800,665, filed 11/22/85, now abandoned.

BACKGROUND OF THE INVENTION (1) Field of the Invention

This invention relates to novel 3(2H)-pyridazinone derivatives; preparation thereof; insecticidal, acaricidal, nematicidal, fungicidal compositions for agricultural and horticultural uses; and expellent compositions for ticks parasitic on animals; said compositions containing said derivatives as an active ingredient.

(2) Description of the Prior Art

The present inventors have previously found that a part of 3(2H)-pyridazinone derivatives of the formula (IV) below has agricultural and horticultural insecticidal, acaricidal, nematicidal, fungicidal actions (refer to Laid-open European patent specification No. 0088384 and Laid-open Japanese patent specification Sho 60-4173).

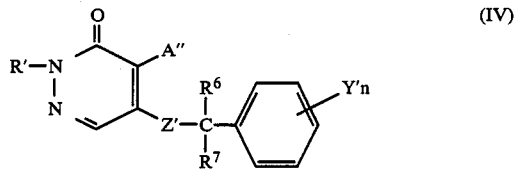

(IV)

wherein, for example, R' denotes an alkyl, A" denotes a halogen atom, $R^6$ and $R^7$ denote hydrogen atom or a lower alkyl, and Z' denotes oxygen or sulfur atom.

The most important features of these known compounds residues in that a benzyl derivative is bonded to the Z' atom located at the 5-position of a 3(2H)-pyridazinone.

Also, there is disclosed in Japanese Patent Publication Sho 38-7998 a known Compound A of the formula:

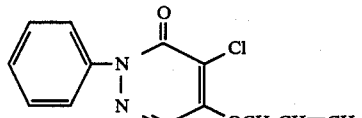

(known Compound A)

as one of the 3(2H)-pyridazinone derivatives of the general formula (V):

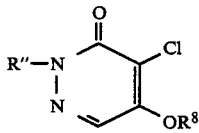

(V)

This Compound A has phenyl group bonded to the nitrogen atom at 2-position of the 3(2H)-pyridazinone and is described as an agricultural drug which affects the growth of plants. Thus, the Compound A is totally different from the compounds of the present invention which are used as agricultural and horticultural insecticidal, acaricidal, nematicidal, fungicidal compositions and expellent compositions for ticks parasitic on animals.

The present inventors have conducted intensive research on the preparation of the novel compounds of the formula I given below as well as on activities thereof as an agricultural and horticultural drug, and have found that the compounds of the formula I below are useful for the control of agricultural and horticultural insect pests, nematoda, mites and ticks, and the prevention of diseases and for expelling ticks parasitic on animals to accomplish the invention.

SUMMARY OF THE INVENTION

An object of this invention is to provide novel 3(2H)-pyridazinone derivatives which have insecticidal, acaricidal, nematicidal and/or fungicidal activities.

Another object of this invention is to provide a process for preparing such 3(2H)-pyridazinone derivatives.

Further object of this invention is to provide insecticidal, acaricidal, nematicidal, fungicidal compositions containing a 3(2H)-pyridazinone derivative as an active ingredient.

Other objects of this invention will become apparent from the description given below.

The 3(2H)-pyridazinone derivatives according to the invention have the general formula (I):

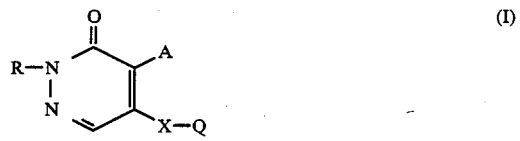

(I)

wherein,

R denotes a straight or branched $C_1$ to $C_6$ alkyl, A denotes a straight or branched $C_1$ to $C_6$ alkyl or a halogen, X denotes oxygen or sulfur atom, Q denotes a group:

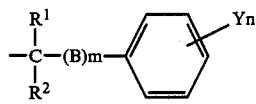

when
A is a straight or branched $C_1$ to $C_6$ alkyl, and
Q denotes a group:

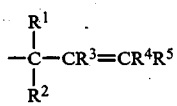

when
A is a halogen atom,
$R^1$ and $R^2$ denote each independently hydrogen, a lower alkyl, a lower haloalkyl, or 4-tert.-butylphenyl,
B denotes $-CR^6=CR^7-$, $-CR^6R^7O-$ or

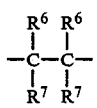

(wherein, $R^6$ and $R^7$ denote each independently hydrogen or a $C_1$ to $C_3$ alkyl)

m is 0 or 1,

Y denotes hydrogen, a halogen, a $C_1$ to $C_6$ alkyl, a cycloalkyl, a cycloalkyloxy, a $C_1$ to $C_6$ alkyloxy, a $C_1$ to $C_6$ alkylthio, a $C_1$ to $C_6$ aklylsulfinyl, a $C_1$ to $C_6$ alkylsulfonyl, a lower haloalkyl, a lower haloalkyloxy, a lower haloalkylthio, a lower alkenyloxy, trimethylsilyl, a lower alkoxycarbonyl, dimethylamino, nitro, cyano, SCN,

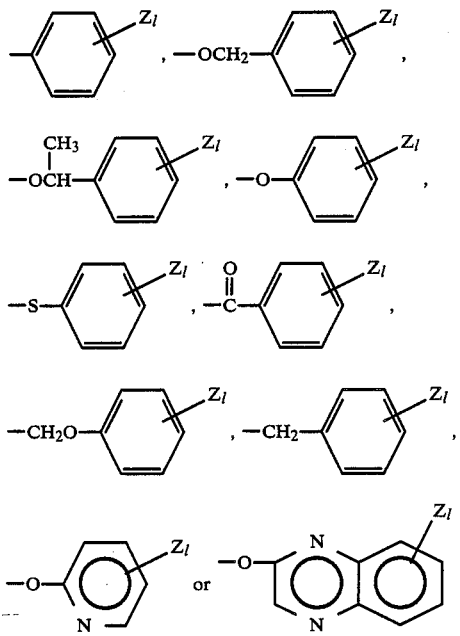

(wherein, Z denotes a halogen, a lower alkyl, a lower alkoxy, a cycloalkyl, a lower haloalkyl, a lower alkoxycarbonyl or nitro and l is 0 or an integer of from 1 to 5, said Z being the same or different when l is an integer of 2 to 5), n is an integer of from 1 to 5, said Y being the same or different when n is an integer of 2 to 5, $R^3$ and $R^4$ denote each independently hydrogen, a halogen, a lower alkyl or 4-methoxyphenyl, or $R^3$ and $R^4$ together form a direct bond so as to form a triple bond between the carbon atoms to which they are linking, and $R^5$ denotes a halogen, a $C_1$ to $C_6$ alkyl, a $C_2$ to $C_6$ alkenyl or

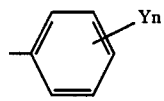

(wherein, Y and n are as defined in the above).

The compounds of the formula (I) can be prepared by reacting a compound of the formula (VI):

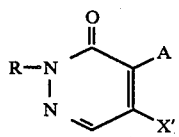

(VI)

with a compound of the formula (VII):

$$X'-Q \qquad (VII)$$

(wherein, X' and X" denote each independently —SH, —OH or a halogen, provided that X" denotes a halogen when X' is —SH or —OH and X" denotes —SH or —OH when X' is a halogen; and R, A and Q are as defined in formula (I)).

The present invention also comprises insecticidal, acaricidal, nematicidal, and/or fungicidal compositions for agricultural and horticultural uses; and compositions for expelling ticks that are parasitic on animals; said compositions containing said derivatives as an active ingredient.

The compounds according to the present invention have excellent insecticidal, acaricidal, nematicidal and/or fungicidal actions and exhibit higher activity than the known compounds of the formula (IV) described above. The compounds of the invention can effectively control organisms which are harmful agriculturally and horticulturally even when applied in a very low drug concentration.

DETAILED DESCRIPTION OF THE INVENTION

The "alkyl" including the alkyl moieties contained in the groups such as "alkyloxy", "alkylthio", "alkylsulfinyl" and "alkylsulfonyl" are a straight or branched alkyl.

The "lower alkyl" including the lower alkyl moieties contained in the groups such as "lower alkyloxy", "lower haloalkyl", "lower haloalkyloxy", "lower haloalkylthio" and "lower alkoxycarbonyl" are usually a straight or branched alkyl of 1 to 6 carbon atoms, preferably of 1 to 4 carbon atoms such as methyl, ethyl, n-propyl, i-propyl, n-butyl, iso-butyl, sec.-butyl or tert.-butyl.

The "lower alkenyl" contained in the lower alkenyloxy is usually a straight or branched alkenyl of 2 to 6 carbon atoms, preferably of 2 to 4 carbon atoms such as ethenyl, n-propenyl, n-propadienyl, i-propenyl, n-butenyl, n-butadienyl, n-butatrienyl, sec.-butenyl, and sec.-butadienyl.

The term "halogen" and halogens contained in the groups such as "haloalkyl", "haloalkyloxy" and "haloalkylthio" mean fluorine, chlorine, bromine, iodine atom or a mixture thereof and are preferably fluorine chlorine or bromine.

The "cycloaklyl" and "cycloalkyloxy" as Y or as a substituent Z have preferably 3 to 6 carbon atoms.

R is preferably a straight or branched alkyl of 2 to 4 carbon atoms, such as ethyl, n-propyl, i-propyl, n-butyl, iso-butyl, sec.-butyl, or tert.-butyl, and most preferably tert.-butyl.

$R^1$ and $R^2$ are preferably hydrogen or methyl.

A is preferably methyl, chlorine or bromine.

The compounds of the formula (I) encompass the compounds of the formula (II):

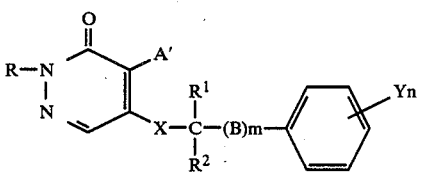

(II)

wherein, A' denotes a straight or branched $C_1$ to $C_6$ alkyl, and R, $R^1$, $R^2$, X, B, Y, m and n are as defined in the formula (I).

The compounds of the formula (II) having the following substituents are important from the viewpoint of pesticidal activities:

The compounds of the formula (II),
wherein
R is tert.-butyl,
A' is methyl,
X is sulfur or oxygen atom,
$R^1$ and $R^2$ are each independently hydrogen or methyl,
B is —$CR^6$=$CR^7$— (wherein, $R^6$ and $R^7$ are each independently hydrogen or methyl),
m is 0 or 1,
Y is hydrogen, a halogen, a straight or branched $C_1$ to $C_6$ alkyl, a $C_3$ to $C_6$ cycloalkyl, a $C_3$ to $C_6$ cycloalkyloxy, a straight or branched $C_1$ to $C_6$ alkyloxy, a straight or branched $C_1$ to $C_6$ haloalkyl, a straight or branched $C_1$ to $C_6$ haloalkyloxy, a straight or branched $C_3$ to $C_6$ alkenyloxy, trimethylsilyl,

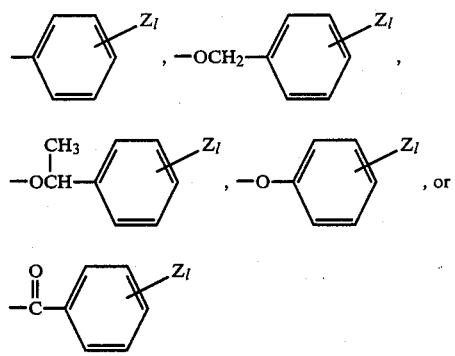

(wherein, Z denotes a halogen, a lower alkyl, a lower alkoxy or a lower haloalkyl and l is 0 or an integer of from 1 to 5, said Z being the same of different when l is an integer of 2 to 5), and
n is an integer of from 1 to 5, said Y being the same or different when n is an integer of 2 to 5.

Among the compounds of the formula (II), the following compounds are most important from the viewpoint of pesticidal activities.

The compounds of the formula:

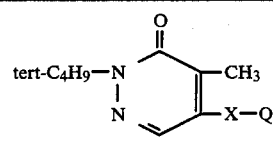

| Compound No. | —X—Q | Compound No. | —X—Q |
|---|---|---|---|
| 36 | —OCH(CH₃)—C₆H₄—C₆H₄—Cl | 140 | —OCH₂—C₆H₄—Si(CH₃)₃ |
| 38 | —S—CH(CH₃)—C₆H₄—C₆H₄—Cl | 141 | —SCH₂—C₆H₄—Si(CH₃)₃ |
| 43 | —S—CH₂—C₆H₄—C₆H₄—F | 143 | —OCH(CH₃)—C₆H₄—C₆H₁₁ |
| 47 | —O—CH₂—C₆H₄—C₆H₅ | 145 | —SCH₂—C₆H₄—C₆H₁₁ |
| 49 | —S—CH₂—C₆H₄—C₆H₅ | 147 | —SCH(CH₃)—C₆H₄—C₆H₁₁ |
| 53 | —OCH₂—C₆H₄—CF₃ | 150 | —SCH₂—C₆H₄—cyclopropyl |

-continued

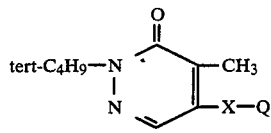

| Compound No. | —X—Q | Compound No. | —X—Q |
|---|---|---|---|
| 55 | —SCH₂—C₆H₄—CF₃ | 157 | —SCH₂—C₆H₄—i-Pro |
| 68 | —SCH₂—C₆H₄—C(O)—C₆H₄—Cl | 159 | —SCH₂—C₆H₄—Bu** |
| 89 | —OCH₂—C₆H₄—O—i-Pro* | 169 | —OCH₂—C₆H₄—t-Bu*** |
| 91 | —SCH₂—C₆H₄—O—Pro | 170 | —SCH₂—C₆H₄—t-Bu |
| 100 | —SCH₂—C₆H₄—O—C₆H₄—CF₃ | 173 | —SCH(CH₃)—C₆H₄—t-Bu |
| 177 | —OCH₂C(CH₃)=CH—C₆H₄—t-Bu | 190 | —SCH(CH₃)CH=CH—C₆H₄—t-Bu |
| 183 | —SCH₂—C₆H₄—C₆H₁₃ | 191 | —SCH₂CH=CH—C₆H₄—t-Bu |
| 186 | —OCH₂C(CH₃)=CH—C₆H₄—C₆H₅ | 196 | —SCH₂CH=CH—C₆H₄—Bu |
| 189 | —SCH₂CH=C(CH₃)—C₆H₄—t-Bu | | |

*"Pro" represents propyl
**"Bu" represents butyl
***"t" represents tertiary

The examples of the compounds of the formula (II) are listed in Table 1.

The compounds of the formula (I) also encompass the compounds of the formula (III):

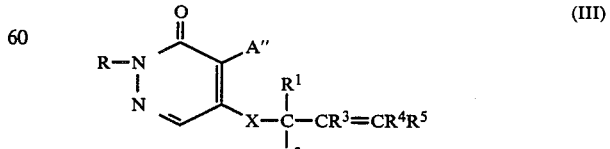

wherein, A″ denotes a halogen and R, R¹, R², X, R³, R⁴ and R⁵ are as defined in formula (I).

The compounds of the formula (III) having the following substituents are important from the viewpoint of pesticidal activities:

The compounds of the formula (III),
wherein
R is tert.-butyl,
A″ is chlorine or bromine,
X is sulfur or oxygen,
$R^1$ and $R^2$ are each independently hydrogen or methyl,
$R^3$ and $R^4$ are each independently hydrogen, a lower alkyl or a halogen, or $R^3$ and $R^4$ together form a direct bond so as to form a triple bond between the carbon atoms to which they are linking,
$R^5$ is

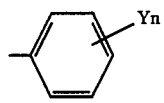

Y is hydrogen, a halogen, a $C_1$ to $C_6$ alkyl, a $C_3$ to $C_6$ cycloaklyl, a $C_3$ to $C_6$ cycloalkyloxy, a $C_1$ to $C_6$ alkyloxy, a $C_1$ to $C_6$ haloalkyl, a $C_1$ to $C_6$ haloalkyloxy, a $C_3$ to $C_6$ alkenyloxy, trimethylsilyl,

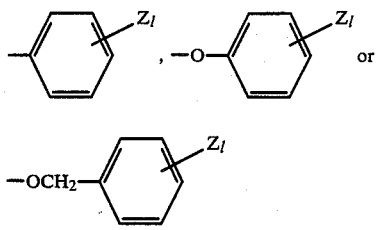

(wherein, Z denotes a halogen, a lower alkyl, a lower alkoxy or a lower haloalkyl and l is 0 or an integer of from 1 to 5, said Z being the same or different when l is an integer of 2 to 5) and
n is an integer of from 1 to 5, said Y being the same or different when n is an integer of 2 to 5.

Among the compounds of the formula (III), the following compounds are most important from the viewpoint of pesticidal activities.

The compounds of the formula:

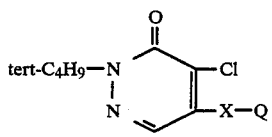

| Compound No. | —X—Q | Compound No. | —X—Q |
|---|---|---|---|
| 248 | —SCH₂CH=CH—⟨C₆H₄⟩—Cl | 382 | —SCH₂CH=CH—⟨C₆H₄⟩—t-Bu*** |
| 255 | —SCH(CH₃)CH=CH—⟨C₆H₄⟩—Cl | 383 | —OCH₂CH=CH—⟨C₆H₄⟩—t-Bu |
| 301 | —OCH₂CH=CH—⟨C₆H₃(Cl)⟩—Cl | 384 | —SCH(CH₃)CH=CH—⟨C₆H₄⟩—t-Bu |
| 311 | —SCH₃CH=CH—⟨C₆H₃(Cl)⟩—Cl | 388 | —OCH₂C(CH₃)=CH—⟨C₆H₄⟩—t-Bu |
| 328 | —OCH₂CH=CH—⟨C₆H₄⟩—CH₃ | 442 | —SCH₂CH=CH—⟨C₆H₄⟩—CF₃ |
| 335 | —SCH₂CH=CH—⟨C₆H₃(CH₃)₂⟩ | 463 | —SCH(CH₃)CH=CH—⟨C₆H₄⟩—C₆H₅ |

-continued

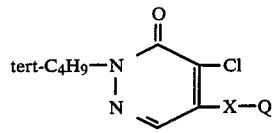

| Compound No. | —X—Q | Compound No. | —X—Q |
|---|---|---|---|
| 363 | 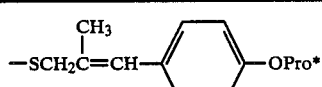 | 464 | 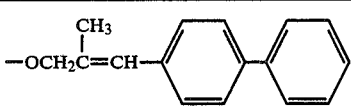 |
| 374 | 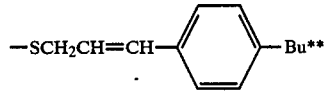 | | |

*"Pro" represents propyl.
**"Bu" represents butyl.
***"t" represents tertiary.

The examples of the compounds of the formula (III) are listed in Tables 2 and 3 below.

Incidentally, it should be understood that the compounds listed in Tables 1 through 3 are only illustrative and not to restrict the present invention.

A compound of the invention containing asymmetric carbon atom(s) includes optically active (+) compound and (−) compound.

[In Tables 1 through 3, "Me" denotes methyl, "Et" denotes ethyl, "Pro" denotes propyl, "Bu" denotes butyl, "Pen" denotes pentyl, "Hex" denotes hexyl, "t" denotes tertiary, "i" denotes iso, and "s" denotes secondary.]

TABLE 1

The compounds of the formula:

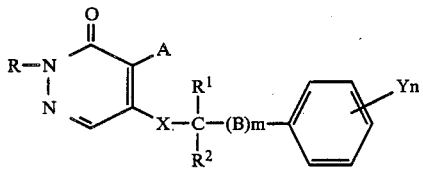

| Comp. No. | R | A | X | R¹ | R² | (B)m | Yn | M.P. (°C.) |
|---|---|---|---|---|---|---|---|---|
| 1 | t-Bu | Et | O | H | H | m = 0 | H | Oil |
| 2 | Et | Et | S | H | H | " | 4-F | |
| 3 | t-Bu | Me | O | H | H | " | 4-F | 65.0~66.5 |
| 4 | t-Bu | Me | O | Me | H | " | 4-F | $N_D^{20}$ 1.5375 |
| 5 | t-Bu | Me | S | H | H | " | 4-F | 64.5~68.5 |
| 6 | Et | Et | S | H | H | " | 4-Cl | |
| 7 | t-Bu | Et | O | H | H | " | 4-Cl | 86.0~88.0 |
| 8 | t-Bu | Et | S | H | H | " | 4-Cl | |
| 9 | t-Bu | Pro | O | H | H | " | 4-Cl | Oil |
| 10 | t-Bu | Pro | S | H | H | m = 0 | 4-Cl | |
| 11 | t-Bu | Me | O | H | H | " | 4-Cl | 102.0~104.0 |
| 12 | t-Bu | Me | O | H | H | CH₃<br>\|<br>—C=CH— | 4-Cl | |
| 13 | t-Bu | Me | S | H | H | m = 0 | 4-Cl | |
| 14 | t-Bu | Me | S | Me | H | " | 4-Cl | 121.0~123.5 |
| 15 | t-Bu | Me | S | H | H | " | 3-Br | |
| 16 | t-Bu | Me | O | Me | H | " | 4-Br | |
| 17 | t-Bu | Me | S | H | H | " | 4-Br | 86.0~86.5 |
| 18 | Et | Et | O | H | H | " | 4-Br | |
| 19 | t-Bu | Me | S | H | H | " | 4-I | |
| 20 | t-Bu | Me | O | H | H | " | 2,3,4,5,6-F₅ | |
| 21 | t-Bu | Me | S | H | H | " | 2,3,4,5,6-F₅ | |
| 22 | t-Bu | Me | S | H | H | m = 0 | 2,4-Cl₂ | 103.0~104.5 |
| 23 | t-Bu | Me | O | H | H | " | 3,4-Cl₂ | |
| 24 | t-Bu | Me | S | H | H | " | 3,4-Cl₂ | 99.5~101.0 |
| 25 | t-Bu | Me | S | H | H | CH₃<br>\|<br>—C=CH— | 3,4-Cl₂ | |

TABLE 1-continued

The compounds of the formula:

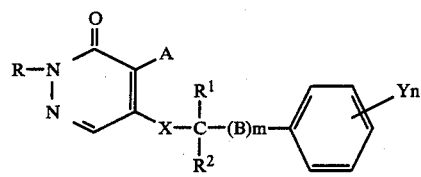

| Comp. No. | R | A | X | R¹ | R² | (B)m | Yn | M.P. (°C.) |
|---|---|---|---|---|---|---|---|---|
| 26 | t-Bu | Me | S | H | H | m = 0 | 3,4-Cl$_2$ | |
| 27 | t-Bu | Me | S | H | H | " | 2-F, 4-CF$_3$ | |
| 28 | t-Bu | Me | S | H | H | " | 2,4-Me$_2$ | 104.0~108.0 |
| 29 | t-Bu | Me | S | H | H | " | 2,5-Me$_2$ | Oil (N$_D^{21}$ 1.5891) |
| 30 | t-Bu | Me | S | H | H | " | 3-OMe, 4-Cl | Oil (N$_D^{20}$ 1.6016) |
| 31 | t-Bu | Me | S | H | H | " | 3-OMe, 4-t-Bu | Oil (N$_D^{20}$ 1.5790) |
| 32 | t-Bu | Me | S | H | H | " | 2,4-(CH$_3$)$_2$-phenyl | 183.5~186.0 |
| 33 | t-Bu | Me | S | H | H | " | 2,4-Cl$_2$-phenyl | Oil |
| 34 | t-Bu | Me | S | H | H | m = 0 | 4-Br-phenyl | 83.0~95.0 |
| 35 | Et | Et | S | H | H | " | 4-Cl-phenyl | |
| 36 | t-Bu | Me | O | Me | H | " | 4-Cl-phenyl | Oil (N$_D^{20}$ 1.5883) |
| 37 | t-Bu | Me | O | H | H | " | 4-Cl-phenyl | |
| 38 | t-Bu | Me | S | Me | H | " | 4-Cl-phenyl | 206.0~211.0 |
| 39 | t-Bu | Me | S | H | H | —C(CH$_3$)=CH— | 4-Cl-phenyl | |
| 40 | t-Bu | i-Pro | S | H | H | m = 0 | 4-Cl-phenyl | |

TABLE 1-continued
The compounds of the formula:
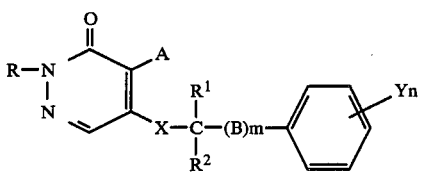
| Comp. No. | R | A | X | R¹ | R² | (B)m | Yn | M.P. (°C.) |
|---|---|---|---|---|---|---|---|---|
| 41 | t-Bu | Et | S | H | H | " | 4-C₆H₄-Cl | |
| 42 | t-Bu | i-Bu | S | H | H | " | 4-C₆H₄-Cl | |
| 43 | t-Bu | Me | S | H | H | " | 4-C₆H₄-F | 90.5~93.5 |
| 44 | Et | Et | S | H | H | " | 4-C₆H₅ | |
| 45 | i-Pro | Me | S | H | H | " | 4-C₆H₅ | Oil ($N_D^{20}$ 1.6435) |
| 46 | t-Pen | Me | S | H | H | m = 0 | 4-C₆H₅ | |
| 47 | t-Bu | Me | O | H | H | " | 4-C₆H₅ | 170.5~174.0 |
| 48 | t-Bu | Me | O | Me | H | " | 4-C₆H₅ | |
| 49 | t-Bu | Me | S | H | H | " | 4-C₆H₅ | 112.0~115.0 |
| 50 | t-Bu | Me | S | H | H | $-\overset{CH_3}{\underset{}{C}}=CH-$ | 4-C₆H₅ | |
| 51 | s-Bu | Me | O | H | H | m = 0 | 4-C₆H₅ | |
| 52 | Et | Et | O | H | H | " | 4-CF₃ | |
| 53 | t-Bu | Me | O | H | H | " | 4-CF₃ | 113.0~115.5 |

TABLE 1-continued

The compounds of the formula:

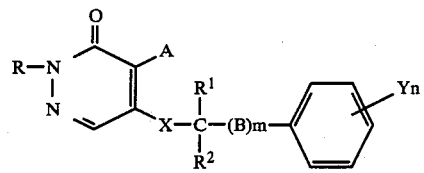

| Comp. No. | R | A | X | R¹ | R² | (B)m | Yn | M.P. (°C.) |
|---|---|---|---|---|---|---|---|---|
| 54 | t-Bu | Me | O | H | H | $-\underset{\underset{CH_3}{\vert}}{C}=CH-$ | 4-CF$_3$ | |
| 55 | t-Bu | Me | S | H | H | m = 0 | 4-CF$_3$ | 61.5~64.0 |
| 56 | Hex | Me | S | H | H | " | 4-CF$_3$ | |
| 57 | t-Bu | Me | O | H | H | " | 3-CF$_3$ | |
| 58 | t-Bu | Me | S | H | H | m = 0 | 4-C(CH$_3$)$_2$CH$_2$Cl | |
| 59 | t-Bu | Me | S | H | H | " | 4-CH$_2$O— (2-Cl phenyl) | 110.5~114.5 |
| 60 | t-Bu | Me | S | H | H | " | 4-CH$_2$O— (4-t-Bu phenyl) | 89.0~90.0 |
| 61 | t-Bu | Me | S | H | H | " | 3-CH$_3$, 4- (2-Cl, 4-Cl phenyl) | Oil |
| 62 | t-Bu | Me | O | H | H | " | 4-CO— (2-Cl, 4-Cl phenyl) | |
| 63 | t-Bu | Me | O | H | H | " | 4-CO— (3-Cl, 4-Cl phenyl) | |
| 64 | t-Bu | Me | O | H | H | " | 4-CO— (2-Cl phenyl) | |
| 65 | t-Bu | Me | O | H | H | " | 4-CO— (4-CF$_3$ phenyl) | |
| 66 | t-Bu | Me | O | H | H | " | 4-CO— (4-COOCH$_3$ phenyl) | |
| 67 | t-Bu | Me | O | H | H | " | 4-CO— (4-Cl phenyl) | |

TABLE 1-continued
The compounds of the formula:
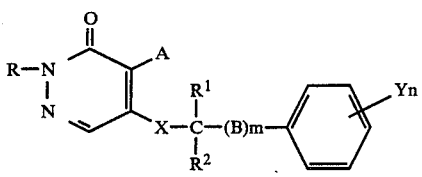
| Comp. No. | R | A | X | $R^1$ | $R^2$ | (B)m | Yn | M.P. (°C.) |
|---|---|---|---|---|---|---|---|---|
| 68 | t-Bu | Me | S | H | H | " | 4-CO—⟨C₆H₄⟩—Cl | 149.5~151.0 |
| 69 | Et | Et | O | H | H | " | 4-CO—⟨C₆H₄⟩—Cl | |
| 70 | Et | Me | O | H | H | m = 0 | 4-CO—⟨C₆H₄⟩—Cl | |
| 71 | Et | Me | S | H | H | " | 4-CO—⟨C₆H₄⟩—Cl | |
| 72 | Me | Me | O | H | H | " | 4-CO—⟨C₆H₄⟩—Cl | |
| 73 | Me | Me | S | H | H | " | 4-CO—⟨C₆H₄⟩—Cl | |
| 74 | Pro | Me | O | H | H | " | 4-CO—⟨C₆H₄⟩—Cl | |
| 75 | Pro | Me | S | H | H | " | 4-CO—⟨C₆H₄⟩—Cl | |
| 76 | Bu | Me | O | H | H | " | 4-CO—⟨C₆H₄⟩—Cl | |
| 77 | Bu | Me | S | H | H | " | 4-CO—⟨C₆H₄⟩—Cl | |
| 78 | t-Bu | Me | O | H | H | " | 4-CO—⟨C₆H₄⟩—$NO_2$ | |

TABLE 1-continued

The compounds of the formula:

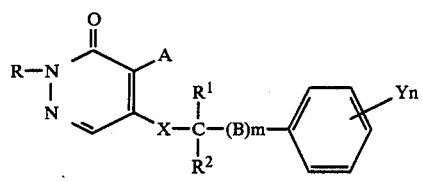

| Comp. No. | R | A | X | R¹ | R² | (B)m | Yn | M.P. (°C.) |
|---|---|---|---|---|---|---|---|---|
| 79 | t-Bu | Me | S | H | H | " | 4-CO—⟨C₆H₄⟩—OCH₃ | |
| 80 | t-Bu | Me | O | H | H | " | 4-CO—⟨C₆H₄⟩—OCH₃ | |
| 81 | t-Bu | Me | O | H | H | " | 4-CO—⟨C₆H₄⟩—OC₃H₇ | |
| 82 | t-Bu | Me | O | H | H | m = 0 | 4-COOCH₃ | 107.0~109.0 |
| 83 | t-Bu | Me | S | H | H | " | 4-COOC₂H₅ | |
| 84 | t-Bu | Me | O | H | H | " | 4-CN | |
| 85 | t-Bu | Me | S | H | H | " | 4-CN | |
| 86 | t-Bu | Me | S | H | H | " | 4-N(CH₃)₂ | 80.0~86.0 |
| 87 | t-Bu | Me | S | H | H | " | 3-NO₂, 4-OC₄H₉ | 94.5~96.0 |
| 88 | t-Bu | Me | S | H | H | " | 4-OC₂H₅ | |
| 89 | t-Bu | Me | O | H | H | " | 4-O—i-Pro | Oil (N$_D^{20}$ 1.5490) |
| 90 | t-Bu | Me | O | H | H | " | 4-OC₃H₇ | |
| 91 | t-Bu | Me | S | H | H | " | 4-OC₃H₇ | Oil (N$_D^{20}$ 1.5810) |
| 92 | t-Bu | Me | O | H | H | " | 4-O—i-Bu | |
| 93 | t-Bu | Me | S | H | H | " | 4-O—i-Bu | |
| 94 | Et | Et | O | Me | H | m = 0 | 4-O—i-Bu | |
| 95 | t-Bu | Me | O | H | H | " | 4-OC₅H₁₁ | Oil |
| 96 | t-Bu | Me | O | H | H | " | 4-O—s-Bu | |
| 97 | t-Bu | Me | O | H | H | " | 4-O—⟨C₆H₄⟩—Cl | |
| 98 | t-Bu | Me | S | H | H | " | 4-O—⟨C₆H₄⟩—Cl | 134.0~137.0 |
| 99 | t-Bu | Me | O | H | H | " | 4-O—⟨C₆H₄⟩—CF₃ | |
| 100 | t-Bu | Me | S | H | H | " | 4-O—⟨C₆H₄⟩—CF₃ | 123.0~124.0 |
| 101 | Et | Et | O | Me | H | " | 4-O—⟨C₆H₄⟩—CF₃ | |

TABLE 1-continued
The compounds of the formula:
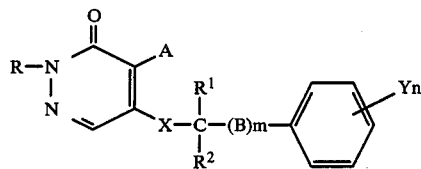
| Comp. No. | R | A | X | R¹ | R² | (B)m | Yn | M.P. (°C.) |
|---|---|---|---|---|---|---|---|---|
| 102 | t-Bu | Me | S | H | H | " | 4-O—⟨C₆H₄⟩—CH₂Cl | |
| 103 | t-Bu | Et | O | H | H | " | 4-S—⟨C₆H₄⟩—CF₃ | |
| 104 | t-Bu | Me | S | H | H | " | 4-S—⟨C₆H₄⟩—CF₃ | |
| 105 | t-Bu | Me | O | H | H | " | 4-O—⟨pyridine, Cl, CF₃⟩ | |
| 106 | t-Bu | Me | O | H | H | m = 0 | 4—⟨quinoxaline, Cl⟩ | |
| 107 | t-Bu | Me | O | H | H | " | 4-OCH₂—⟨C₆H₄⟩—CH₃ | Oil |
| 108 | t-Bu | Me | O | H | H | " | 4-OCH₂—⟨C₆H₄⟩—F | 117.0~119.0 |
| 109 | t-Bu | Me | S | H | H | " | 4-OCH₂—⟨C₆H₄⟩—F | |
| 110 | t-Bu | Me | O | H | H | " | 4-OCH₂—⟨C₆H₄⟩—Cl, Cl | |
| 111 | t-Bu | Me | O | H | H | " | 4-OCH₂—⟨C₆H₄⟩—F, F | |

TABLE 1-continued

The compounds of the formula:

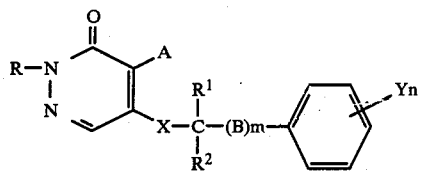

| Comp. No. | R | A | X | R$^1$ | R$^2$ | (B)m | Yn | M.P. (°C.) |
|---|---|---|---|---|---|---|---|---|
| 112 | t-Bu | Me | O | H | H | " | 4-OCH$_2$–(2-Cl-phenyl) | |
| 113 | t-Bu | Me | O | H | H | " | 4-OCH$_2$–(4-CF$_3$-phenyl) | |
| 114 | t-Bu | Me | S | H | H | " | 4-OCH$_2$–(4-CF$_3$-phenyl) | |
| 115 | t-Bu | Me | O | H | H | " | 3-OCH$_2$–(3-CF$_3$-phenyl) | |
| 116 | t-Bu | Me | O | H | H | " | 4-OCH$_2$–(4-Cl-phenyl) | |
| 117 | t-Bu | Me | S | H | H | " | 4-OCH$_2$–(4-Cl-phenyl) | |
| 118 | t-Bu | Me | O | H | H | m = 0 | 4-OCH$_2$–(4-CH$_3$-phenyl) | |
| 119 | t-Bu | Me | O | H | H | " | 4-OCH$_2$–(cyclohexyl-phenyl) | |
| 120 | t-Bu | Me | O | H | H | " | 4-OCH$_2$–phenyl | |
| 121 | t-Bu | Me | S | H | H | " | 4-OCH$_2$–phenyl | |
| 122 | t-Bu | Me | O | H | H | " | 4-OCH$_2$C(CH$_3$)=CH$_2$ | |
| 123 | t-Bu | Me | S | H | H | " | 4-OCH$_2$C(CH$_3$)=CH$_2$ | |
| 124 | t-Bu | Me | O | H | H | " | 4-OCH$_2$CH$_2$CH$_2$Cl | |

TABLE 1-continued

The compounds of the formula:

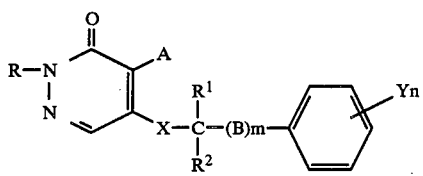

| Comp. No. | R | A | X | R¹ | R² | (B)m | Yn | M.P. (°C.) |
|---|---|---|---|---|---|---|---|---|
| 125 | t-Bu | Me | O | H | H | " | 4-O-C₆H₁₁ | |
| 126 | t-Bu | Me | S | H | H | " | 4-O-C₆H₁₁ | |
| 127 | t-Bu | Me | O | H | H | " | 4-OCH₂CF₃ | |
| 128 | t-Bu | Me | S | H | H | " | 4-OCH₂CF₃ | |
| 129 | t-Bu | Me | O | H | H | " | 4-OCF₂CF₂H | |
| 130 | t-Bu | Me | O | H | H | m = 0 | 4-OCF₃ | |
| 131 | t-Bu | Me | S | H | H | " | 4-OCF₃ | |
| 132 | t-Bu | Et | O | H | H | " | 4-OCH₃ | 80.5~82.0 |
| 133 | t-Bu | Me | O | H | H | " | 4-S—i-Pro | |
| 134 | t-Bu | Me | S | H | H | " | 4-S—i-Pro | |
| 135 | t-Bu | Me | S | H | H | " | 4-SO—i-Pro | |
| 136 | t-Bu | Me | S | H | H | " | 4-SO₂—i-Pro | |
| 137 | t-Bu | Me | O | H | H | " | 4-SCHF₂ | |
| 138 | t-Bu | Me | O | H | H | " | 4-SCF₃ | |
| 139 | t-Bu | Me | O | H | H | " | 4-SCN | |
| 140 | t-Bu | Me | O | H | H | " | 4-Si(CH₃)₃ | 93.5~95.5 |
| 141 | t-Bu | Me | S | H | H | " | 4-Si(CH₃)₃ | 74.0~78.0 |
| 142 | t-Bu | Me | S | H | H | m = 0 | 4-CH₂-C₆H₅ | |
| 143 | t-Bu | Me | O | Me | H | " | 4-C₆H₁₁ | 73.0~76.0 |
| 144 | t-Bu | Me | O | H | H | " | 4-C₆H₁₁ | |
| 145 | t-Bu | Me | S | H | H | " | 4-C₆H₁₁ | 109.0~112.0 |
| 146 | t-Bu | Et | S | H | H | " | 4-C₆H₁₁ | |
| 147 | t-Bu | Me | S | Me | H | " | 4-C₆H₁₁ | Oil (N_D^20 1.3238) |
| 148 | t-Bu | Me | S | H | H | " | 4-C₆H₁₀-CH₃ | |

TABLE 1-continued

The compounds of the formula:

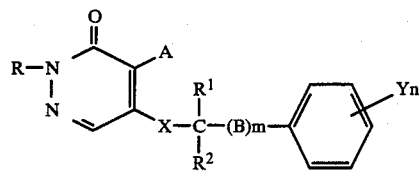

| Comp. No. | R | A | X | R¹ | R² | (B)m | Yn | M.P. (°C.) |
|---|---|---|---|---|---|---|---|---|
| 149 | t-Bu | Me | O | H | H | " | 4-cyclopropyl | |
| 150 | t-Bu | Me | S | H | H | " | 4-cyclopropyl | Oil ($N_D^{20}$ 1.5944) |
| 151 | t-Bu | Me | O | H | H | " | 4-cyclopentyl | |
| 152 | t-Bu | Pro | O | H | H | " | 4-$CH_3$ | Oil |
| 153 | t-Bu | Et | O | H | H | " | 4-$CH_3$ | 90.0~91.0 |
| 154 | t-Bu | Et | S | H | H | m = 0 | 4-$CH_3$ | |
| 155 | t-Bu | Me | O | H | H | " | 4-$CH_3$ | |
| 156 | t-Bu | Me | S | H | H | " | 4-$CH_3$ | 104.0~107.0 |
| 157 | t-Bu | Me | S | H | H | " | 4-i-Pro | Oil ($N_D^{20}$ 1.5801) |
| 158 | t-Bu | Me | O | H | H | " | 4-$C_4H_9$ | |
| 159 | t-Bu | Me | S | H | H | " | 4-$C_4H_9$ | Oil ($N_D^{20}$ 1.5746) |
| 160 | t-Bu | Et | O | H | H | " | 4-t-Bu | 105.0~106.5 |
| 161 | Et | Et | O | H | H | " | 4-t-Bu | |
| 162 | t-Bu | Bu | S | H | H | " | 4-t-Bu | Oil ($N_D^{20}$ 1.5550) |
| 163 | t-Bu | Hex | S | H | H | " | 4-t-Bu | |
| 164 | Et | Me | S | H | H | " | 4-t-Bu | Oil ($N_D^{20}$ 1.3823) |
| 165 | Et | Et | S | H | H | " | 4-t-Bu | |
| 166 | i-Pro | Me | S | H | H | m = 0 | 4-t-Bu | 105.0~107.0 |
| 167 | Et | Et | S | Me | H | " | 4-t-Bu | |
| 168 | i-Pro | Me | S | Me | H | " | 4-t-Bu | |
| 169 | t-Bu | Me | O | H | H | " | 4-t-Bu | 104.0~105.0 |
| 170 | t-Bu | Me | S | H | H | " | 4-t-Bu | 91.0~92.0 |
| 171 | t-Bu | i-Pro | S | H | H | " | 4-t-Bu | |
| 172 | t-Bu | s-Bu | O | H | H | " | 4-t-Bu | |
| 173 | t-Bu | Me | S | Me | H | " | 4-t-Bu | Oil ($N_D^{20}$ 1.5597) |
| 174 | t-Bu | Me | S | Et | H | " | 4-t-Bu | Oil ($N_D^{20}$ 1.5630) |
| 175 | t-Bu | Me | O | $CF_3$ | H | " | 4-t-Bu | semi-solid |
| 176 | t-Bu | Me | O | H | H | —CH=CH— | 4-t-Bu | 89.0~90.5 |
| 177 | t-Bu | Me | O | H | H | $\overset{CH_3}{\underset{|}{-C=CH-}}$ | 4-t-Bu | 89.0~91.0 |
| 178 | t-Bu | Me | S | H | H | $\overset{CH_3}{\underset{|}{-C=CH-}}$ | 4-t-Bu | |
| 179 | t-Bu | Me | S | H | H | —$CH_2$O— | 4-t-Bu | 84.0~85.0 |
| 180 | t-Bu | Me | O | H | 4-t-Bu-phenyl | m = 0 | 4-t-Bu | 164.5~172.0 |
| 181 | t-Bu | Me | S | H | 4-t-Bu-phenyl | " | 4-t-Bu | 63.5~66.0 |

TABLE 1-continued

The compounds of the formula:

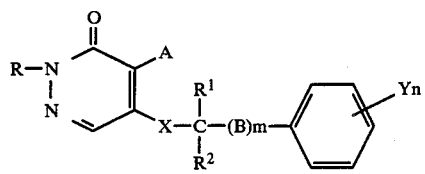

| Comp. No. | R | A | X | R¹ | R² | (B)m | Yn | M.P. (°C.) |
|---|---|---|---|---|---|---|---|---|
| 182 | t-Bu | Me | S | H | H | " | 4-t-Amyl | |
| 183 | t-Bu | Me | S | H | H | " | 4-$C_6H_{13}$ | Oil |
| 184 | t-Bu | Me | S | H | H | —CH=CH— | 2-Bu | Oil |
| 185 | t-Bu | Me | S | Me | H | —CH=CH— | 4-Cl | Oil |
| 186 | t-Bu | Me | O | H | H | $-\overset{CH_3}{\underset{}{C}}=CH-$ | 4-Ph | 110.1~117.2 |
| 187 | t-Bu | Me | O | H | H | m = 0 | 4-OCH$_2$CF$_2$CF$_2$H | |
| 188 | t-Bu | Me | S | H | H | " | 4-OCH$_2$CF$_2$CF$_2$H | |
| 189 | t-Bu | Me | S | H | H | $-\overset{CH_3}{\underset{}{CH}}=CH-$ | 4-t-Bu | Oil |
| 190 | t-Bu | Me | S | Me | H | —CH=CH— | 4-t-Bu | Oil |
| 191 | t-Bu | Me | S | H | H | —CH=CH— | 4-t-Bu | Oil |
| 192 | t-Bu | Me | O | H | H | m = 0 | 4-OCH(CF$_3$)$_2$ | |
| 193 | t-Bu | Me | S | H | H | " | 4-OCH(CF$_3$)$_2$ | |
| 194 | t-Bu | Me | O | H | H | " | 4-OCH$_2$CF$_2$CF$_3$ | |
| 195 | t-Bu | Me | S | H | H | " | 4-OCH$_2$CF$_2$CF$_3$ | |
| 196 | t-Bu | Me | S | H | H | —CH=CH— | 4-Bu | Oil |
| 197 | t-Bu | Me | O | H | H | m = 0 | 4-OCH(CH$_3$)-C$_6$H$_4$-4-Cl | 131.0~133.7 |
| 198 | t-Bu | Me | S | H | H | —CH=CH— | 2-Me, 4-Pen | |
| 199 | t-Bu | Me | O | Me | H | m = 0 | 4-t-Bu | |

TABLE 2

The compounds of the formula:

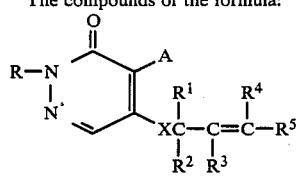

| Comp. No. | R | A | X | R¹ | R² | R³ | R⁴ | R⁵ | M.P. (° C.) |
|---|---|---|---|---|---|---|---|---|---|
| 201 | t-Bu | Cl | S | H | H | H | H | Me | 72.0~75.0 |
| 202 | t-Bu | Cl | O | H | H | H | H | Me | 89.0~90.5 |
| 203 | t-Bu | Br | O | H | H | H | H | Me | |
| 204 | Me | Cl | O | H | H | H | Me | Me | |
| 205 | Et | Cl | O | H | H | H | Me | Me | 72.0~73.0 |
| 206 | Et | Cl | S | H | H | H | Me | Me | |
| 207 | i-Pro | Cl | O | H | H | H | Me | Me | |
| 208 | t-Bu | Cl | O | H | H | H | Me | Me | 75.0~76.0 |
| 209 | t-Bu | Cl | O | H | H | H | H | Et | |
| 210 | t-Bu | Cl | O | H | H | H | H | Pro | |
| 211 | t-Bu | Br | O | H | H | H | H | Pro | |
| 212 | t-Bu | Cl | O | H | H | H | H | i-Bu | |
| 213 | t-Bu | Cl | O | H | H | H | H | Hex | |
| 214 | Pro | Cl | S | H | H | H | Me | —(CH$_2$)$_2$CH=C(CH$_3$)$_2$ | 61.0~63.5 |
| 215 | t-Bu | Cl | O | H | H | H | Me | —(CH$_2$)$_2$CH=C(CH$_3$)$_2$ | Oil |
| 216 | t-Bu | Cl | S | H | H | H | Me | —(CH$_2$)$_2$CH=C(CH$_3$)$_2$ | Oil |
| 217 | t-Bu | Br | O | H | H | H | Me | —(CH$_2$)$_2$CH=C(CH$_3$)$_2$ | |

TABLE 2-continued
The compounds of the formula:
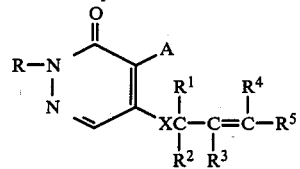
| Comp. No. | R | A | X | R¹ | R² | R³ | R⁴ | R⁵ | M.P. (° C.) |
|---|---|---|---|---|---|---|---|---|---|
| 218 | t-Bu | Cl | O | H | H | Me | H | -CH(CH₃)CH₂CH=CH₂ | |
| 219 | t-Bu | Cl | O | Me | H | H | H | Me | |
| 220 | t-Bu | Cl | O | Et | H | H | H | Me | |
| 221 | t-Bu | Cl | O | Pro | H | H | H | Me | |
| 222 | Me | Cl | S | H | H | H | H | Ph | |
| 223 | Me | Cl | O | H | H | H | H | Ph | |
| 224 | Et | Br | O | H | H | H | H | Ph | 117.0~118.5 |
| 225 | t-Bu | Cl | S | H | H | Cl | H | Ph | |
| 226 | t-Bu | Cl | O | H | H | Cl | H | Ph | |
| 227 | t-Bu | Cl | O | H | H | H | H | Ph | 127.0~129.0 |
| 228 | t-Bu | Cl | O | Me | H | H | H | Ph | 128.0~130.0 |
| 229 | t-Bu | Cl | S | Me | H | H | H | Ph | 126.0~128.0 |
| 230 | t-Bu | Cl | S | H | H | H | Me | Ph | Oil $N_D^{20}$ = 1.6133 |
| 231 | t-Bu | Cl | O | H | H | Me | H | Ph | |

TABLE 2-continued
The compounds of the formula:
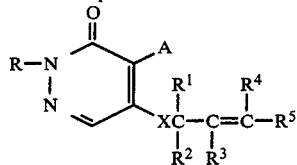
| Comp. No. | R | A | X | R¹ | R² | R³ | R⁴ | R⁵ | M.P. (°C.) |
|---|---|---|---|---|---|---|---|---|---|
| 232 | t-Bu | Cl | S | Me | H | Me | H | phenyl | |
| 233 | Et | Cl | S | H | H | Me | H | 2-F-phenyl | |
| 234 | Et | Br | S | H | H | Me | H | 2-F-phenyl | |
| 235 | t-Bu | Cl | O | H | H | H | H | 2-F-phenyl | |
| 236 | t-Bu | Cl | S | H | H | Me | H | 2-F-phenyl | |
| 237 | t-Bu | Cl | O | H | H | Me | H | 2-F-phenyl | |
| 238 | t-Bu | Cl | S | H | H | H | H | 4-F-phenyl | |
| 239 | i-Pro | Cl | S | H | H | H | H | 2-Cl-phenyl | |
| 240 | t-Bu | Cl | S | H | H | H | H | 2-Cl-phenyl | 128.0~129.0 |
| 241 | t-Bu | Cl | O | H | H | H | H | 2-Cl-phenyl | Oil |

TABLE 2-continued
The compounds of the formula:
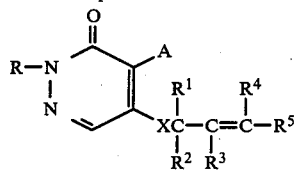
| Comp. No. | R | A | X | R¹ | R² | R³ | R⁴ | R⁵ | M.P. (°C.) |
|---|---|---|---|---|---|---|---|---|---|
| 242 | t-Bu | Cl | S | H | H | Me | H | 2-Cl-C₆H₄ | |
| 243 | t-Bu | Cl | O | H | H | H | H | 3-Cl-C₆H₄ | |
| 244 | t-Bu | Cl | S | H | H | H | H | 3-Cl-C₆H₄ | |
| 245 | t-Bu | Cl | S | H | H | Me | H | 3-Cl-C₆H₄ | |
| 246 | t-Bu | Br | O | H | H | Me | H | 3-Cl-C₆H₄ | |
| 247 | t-Bu | Cl | O | H | H | H | H | 4-Cl-C₆H₄ | 179.0~182.0 |
| 248 | t-Bu | Cl | S | H | H | H | H | 4-Cl-C₆H₄ | 111.0~112.0 |
| 249 | Et | Cl | S | Me | H | H | H | 4-Cl-C₆H₄ | |
| 250 | Et | Br | O | H | H | H | H | 4-Cl-C₆H₄ | |
| 251 | Pro | Cl | S | H | H | H | H | 4-Cl-C₆H₄ | |

TABLE 2-continued
The compounds of the formula:
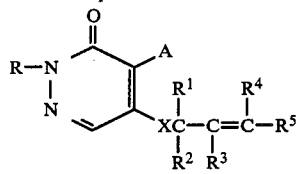
| Comp. No. | R | A | X | R¹ | R² | R³ | R⁴ | R⁵ | M.P. (°C.) |
|---|---|---|---|---|---|---|---|---|---|
| 252 | i-Pro | Cl | S | H | H | H | H | 4-Cl-C₆H₄ | |
| 253 | Bu | Cl | O | H | H | Me | H | 4-Cl-C₆H₄ | |
| 254 | Bu | Cl | S | H | H | Me | H | 4-Cl-C₆H₄ | |
| 255 | t-Bu | Cl | S | Me | H | H | H | 4-Cl-C₆H₄ | 120.2~126.3 |
| 256 | t-Bu | Cl | O | Me | H | H | H | 4-Cl-C₆H₄ | Oil |
| 257 | t-Bu | Cl | S | Et | H | H | H | 4-Cl-C₆H₄ | |
| 258 | t-Bu | Cl | O | Et | H | H | H | 4-Cl-C₆H₄ | |
| 259 | t-Bu | Cl | S | Pro | H | H | H | 4-Cl-C₆H₄ | |
| 260 | t-Bu | Cl | O | Me | H | Me | H | 4-Cl-C₆H₄ | |
| 261 | t-Bu | Cl | S | Me | H | Me | H | 4-Cl-C₆H₄ | |
| 262 | t-Bu | Cl | O | H | H | Et | H | 4-Cl-C₆H₄ | |

TABLE 2-continued
The compounds of the formula:
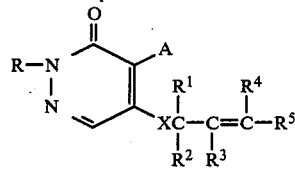
| Comp. No. | R | A | X | R¹ | R² | R³ | R⁴ | R⁵ | M.P. (°C.) |
|---|---|---|---|---|---|---|---|---|---|
| 263 | t-Bu | Cl | S | H | H | Et | H | 4-Cl-C₆H₄ | |
| 264 | t-Bu | Cl | S | H | H | Pro | H | 4-Cl-C₆H₄ | |
| 265 | t-Bu | Cl | S | H | H | i-Pro | H | 4-Cl-C₆H₄ | |
| 266 | i-Pro | Cl | O | H | H | H | Me | 4-Cl-C₆H₄ | |
| 267 | i-Pro | Cl | S | H | H | H | Me | 4-Cl-C₆H₄ | |
| 268 | t-Bu | Cl | O | H | H | H | Me | 4-Cl-C₆H₄ | 123.5~126.6 |
| 269 | t-Bu | Cl | S | H | H | H | Me | 4-Cl-C₆H₄ | Oil |
| 270 | t-Bu | Cl | S | H | H | H | Et | 4-Cl-C₆H₄ | |
| 271 | t-Bu | Cl | S | H | H | H | Pro | 4-Cl-C₆H₄ | |
| 272 | t-Bu | Cl | S | H | H | H | H | 2-Br-C₆H₄ | |
| 273 | t-Bu | Cl | S | H | H | Me | H | 2-Br-C₆H₄ | |

TABLE 2-continued
The compounds of the formula:
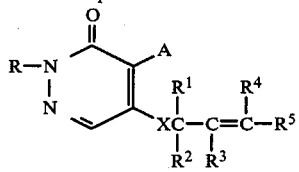
| Comp. No. | R | A | X | R¹ | R² | R³ | R⁴ | R⁵ | M.P. (°C.) |
|---|---|---|---|---|---|---|---|---|---|
| 274 | t-Bu | Cl | O | H | H | Me | H | 2-Br-phenyl | |
| 275 | t-Bu | Cl | S | H | H | Me | H | 3-Br-phenyl | |
| 276 | t-Bu | Cl | O | H | H | Me | H | 3-Br-phenyl | |
| 277 | t-Bu | Cl | S | H | H | H | H | 4-Br-phenyl | 138.0~139.0 |
| 278 | t-Bu | Cl | O | H | H | H | H | 4-Br-phenyl | |
| 279 | t-Bu | Cl | S | H | H | Me | H | 4-Br-phenyl | 77.0~81.0 |
| 280 | t-Bu | Cl | O | H | H | H | H | 2,3-diF-phenyl | |
| 281 | t-Bu | Cl | S | H | H | H | H | 2,3-diF-phenyl | |
| 282 | t-Bu | Cl | S | H | H | Me | H | 2,3-diF-phenyl | |
| 283 | t-Bu | Cl | S | H | H | H | H | 2,4-diF-phenyl | |

TABLE 2-continued
The compounds of the formula:
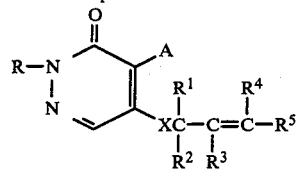
| Comp. No. | R | A | X | R¹ | R² | R³ | R⁴ | R⁵ | M.P. (° C.) |
|---|---|---|---|---|---|---|---|---|---|
| 284 | t-Bu | Cl | S | H | H | Me | H | 2,4-F₂-C₆H₃ | |
| 285 | t-Bu | Cl | O | H | H | Me | H | 2,4-F₂-C₆H₃ | |
| 286 | Et | Cl | O | H | H | H | H | 2,4-F₂-C₆H₃ | |
| 287 | Et | Cl | S | H | H | H | H | 2,4-F₂-C₆H₃ | |
| 288 | t-Bu | Cl | O | H | H | H | H | 2,4-F₂-C₆H₃ | |
| 289 | t-Bu | Cl | S | H | H | H | H | 2,4-F₂-C₆H₃ | |
| 290 | t-Bu | Cl | O | H | H | Me | H | 2,4-F₂-C₆H₃ | |
| 291 | t-Bu | Cl | S | H | H | Me | H | 2,4-F₂-C₆H₃ | |

TABLE 2-continued
The compounds of the formula:
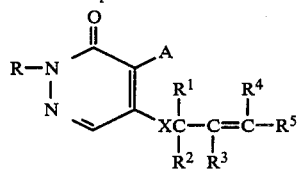
| Comp. No. | R | A | X | R¹ | R² | R³ | R⁴ | R⁵ | M.P. (° C.) |
|---|---|---|---|---|---|---|---|---|---|
| 292 | t-Bu | Br | S | H | H | H | H | 2,4-difluorophenyl | |
| 293 | t-Bu | Cl | S | H | H | H | H | 2,6-difluorophenyl | |
| 294 | t-Bu | Cl | S | H | H | Me | H | 2,6-difluorophenyl | |
| 295 | t-Bu | Cl | O | H | H | Me | H | 3,4-difluorophenyl | |
| 296 | t-Bu | Cl | S | H | H | Me | H | 3,4-difluorophenyl | |
| 297 | t-Bu | Cl | O | H | H | H | H | 2-chloro-6-fluorophenyl | |
| 298 | t-Bu | Cl | S | H | H | H | H | 2-chloro-6-fluorophenyl | |
| 299 | t-Bu | Cl | O | H | H | H | H | 2,6-dichlorophenyl | |

TABLE 2-continued
The compounds of the formula:
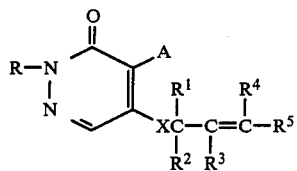
| Comp. No. | R | A | X | R¹ | R² | R³ | R⁴ | R⁵ | M.P. (°C.) |
|---|---|---|---|---|---|---|---|---|---|
| 300 | t-Bu | Cl | S | H | H | H | H | 2,3-Cl₂-C₆H₃ | |
| 301 | t-Bu | Cl | O | H | H | H | H | 2,4-Cl₂-C₆H₃ | 140.0~143.0 |
| 302 | t-Bu | Cl | S | H | H | H | H | 2,4-Cl₂-C₆H₃ | 117.6~118.4 |
| 303 | t-Bu | Cl | S | H | H | Me | H | 2,4-Cl₂-C₆H₃ | 84.0~85.0 |
| 304 | t-Bu | Cl | O | H | H | Me | H | 2,4-Cl₂-C₆H₃ | 105.0~106.0 |
| 305 | i-Pro | Cl | S | H | H | H | H | 2,6-Cl₂-C₆H₃ | |
| 306 | t-Bu | Cl | S | H | H | H | H | 2,6-Cl₂-C₆H₃ | |
| 307 | t-Bu | Cl | O | H | H | Me | H | 2,6-Cl₂-C₆H₃ | |

TABLE 2-continued
The compounds of the formula:
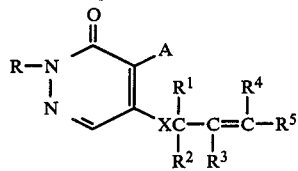
| Comp. No. | R | A | X | R¹ | R² | R³ | R⁴ | R⁵ | M.P. (°C.) |
|---|---|---|---|---|---|---|---|---|---|
| 308 | t-Bu | Cl | S | H | H | Me | H | 2,6-diCl-phenyl | |
| 309 | t-Bu | Br | S | H | H | Me | H | 2,6-diCl-phenyl | |
| 310 | Pro | Cl | O | H | H | H | H | 3,4-diCl-phenyl | |
| 311 | t-Bu | Cl | S | H | H | H | H | 3,4-diCl-phenyl | 128.0~129.0 |
| 312 | t-Bu | Cl | O | H | H | H | H | 3,4-diCl-phenyl | 133.0~134.6 |
| 313 | t-Bu | Cl | S | Me | H | H | H | 3,5-diCl-phenyl | |
| 314 | t-Bu | Cl | O | H | H | Me | H | 3,5-diCl-phenyl | |
| 315 | t-Bu | Cl | S | H | H | Me | H | 3,5-diCl-phenyl | |

TABLE 2-continued
The compounds of the formula:
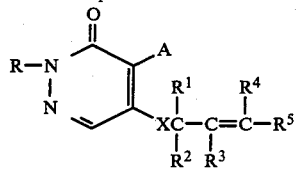
| Comp. No. | R | A | X | R¹ | R² | R³ | R⁴ | R⁵ | M.P. (°C.) |
|---|---|---|---|---|---|---|---|---|---|
| 316 | t-Bu | Cl | S | H | H | H | H | pentafluorophenyl | |
| 317 | t-Bu | Cl | O | H | H | H | H | pentafluorophenyl | |
| 318 | Me | Cl | S | H | H | H | H | o-tolyl | |
| 319 | Me | Cl | O | H | H | H | H | o-tolyl | |
| 320 | Et | Cl | S | H | H | H | H | o-tolyl | |
| 321 | Et | Cl | O | H | H | H | H | o-tolyl | |
| 322 | t-Bu | Cl | O | H | H | H | H | o-tolyl | 135.0~136.5 |
| 323 | t-Bu | Cl | S | H | H | H | H | o-tolyl | 82.0~84.0 |
| 324 | t-Bu | Br | O | H | H | H | H | o-tolyl | |

TABLE 2-continued
The compounds of the formula:
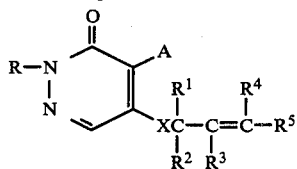
| Comp. No. | R | A | X | R¹ | R² | R³ | R⁴ | R⁵ | M.P. (°C.) |
|---|---|---|---|---|---|---|---|---|---|
| 325 | t-Bu | Cl | S | H | H | Me | H | 2-CH₃-C₆H₄ | |
| 326 | t-Bu | Cl | O | H | H | Me | H | 3-CH₃-C₆H₄ | |
| 327 | t-Bu | Cl | S | H | H | Me | H | 3-CH₃-C₆H₄ | |
| 328 | t-Bu | Cl | O | H | H | H | H | 4-CH₃-C₆H₄ | 137.0~139.5 |
| 329 | t-Bu | Cl | S | Me | H | Me | H | 4-CH₃-C₆H₄ | |
| 330 | t-Bu | Cl | O | H | H | H | H | 2,4-(CH₃)₂-C₆H₃ | 142.5~144.0 |
| 331 | t-Bu | Cl | S | H | H | H | H | 2,4-(CH₃)₂-C₆H₃ | 70.0~72.0 |
| 332 | t-Bu | Cl | S | H | H | Me | H | 2,4-(CH₃)₂-C₆H₃ | |
| 333 | Et | Cl | O | H | H | Me | H | 2,4-(CH₃)₂-C₆H₃ | |

TABLE 2-continued
The compounds of the formula:
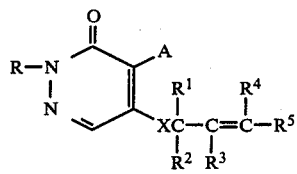
| Comp. No. | R | A | X | R¹ | R² | R³ | R⁴ | R⁵ | M.P. (° C.) |
|---|---|---|---|---|---|---|---|---|---|
| 334 | Et | Cl | S | H | H | Me | H | 2,4-(CH$_3$)$_2$C$_6$H$_3$ | |
| 335 | t-Bu | Cl | S | H | H | H | H | 2,4-(CH$_3$)$_2$C$_6$H$_3$ | Glass |
| 336 | t-Bu | Cl | O | H | H | H | H | 2,4-(CH$_3$)$_2$C$_6$H$_3$ | 142.0~147.0 |
| 337 | t-Bu | Cl | S | H | H | Me | H | 2,4-(CH$_3$)$_2$C$_6$H$_3$ | |
| 338 | t-Bu | Cl | S | Me | H | Me | H | 2,4-(CH$_3$)$_2$C$_6$H$_3$ | |
| 339 | t-Bu | Cl | S | H | H | Et | H | 2,4-(CH$_3$)$_2$C$_6$H$_3$ | |
| 340 | t-Bu | Cl | S | H | H | H | Me | 2,4-(CH$_3$)$_2$C$_6$H$_3$ | Oil N$_D^{20}$ = 1.5880 |

TABLE 2-continued
The compounds of the formula:
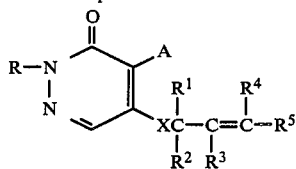
| Comp. No. | R | A | X | R¹ | R² | R³ | R⁴ | R⁵ | M.P. (° C.) |
|---|---|---|---|---|---|---|---|---|---|
| 341 | t-Bu | Cl | O | H | H | H | Me | ![2,4-dimethylphenyl with CH₃ groups] | Oil $N_D^{20} = 1.5604$ |
| 342 | t-Bu | Cl | S | H | H | Me | H | ![2-OCH₃, 4-Br phenyl] | |
| 343 | t-Bu | Cl | O | H | H | H | H | ![2-OCH₃ phenyl] | |
| 344 | t-Bu | Cl | S | H | H | H | H | ![2-OCH₃ phenyl] | |
| 345 | t-Bu | Cl | O | H | H | H | H | ![3-OCH₃ phenyl] | |
| 346 | t-Bu | Cl | S | H | H | H | H | ![3-OCH₃ phenyl] | |
| 347 | Pro | Cl | S | H | H | H | H | ![4-OCH₃ phenyl] | |
| 348 | t-Bu | Cl | S | H | H | H | H | ![4-OCH₃ phenyl] | |
| 349 | t-Bu | Cl | O | H | H | H | H | ![4-OCH₃ phenyl] | |

TABLE 2-continued
The compounds of the formula:
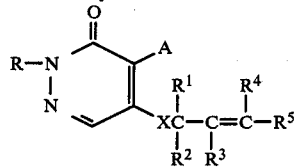
| Comp. No. | R | A | X | R¹ | R² | R³ | R⁴ | R⁵ | M.P. (°C.) |
|---|---|---|---|---|---|---|---|---|---|
| 350 | t-Bu | Cl | S | H | H | 4-MeO-C₆H₄ | H | 4-MeO-C₆H₄ | Oil |
| 351 | t-Bu | Cl | O | H | H | 4-MeO-C₆H₄ | H | 4-MeO-C₆H₄ | Oil |
| 352 | t-Bu | Cl | O | H | H | Me | H | 2,3-(MeO)₂-C₆H₃ | |
| 353 | t-Bu | Cl | S | H | H | Me | H | 2,3-(MeO)₂-C₆H₃ | |
| 354 | t-Bu | Cl | S | H | H | H | H | 2-EtO-C₆H₄ | |
| 355 | t-Bu | Cl | S | H | H | H | H | 4-EtO-C₆H₄ | |
| 356 | t-Bu | Cl | S | H | H | Me | H | 4-EtO-C₆H₄ | |
| 357 | t-Bu | Cl | S | H | H | Me | H | 4-Et-C₆H₄ | 98.0~100.0 |
| 358 | t-Bu | Cl | O | H | H | Me | H | 4-Et-C₆H₄ | 75.0~82.0 |
| 359 | t-Bu | Cl | S | Me | H | Me | H | 4-Et-C₆H₄ | |
| 360 | t-Bu | Cl | S | H | H | H | H | 2-PrO-C₆H₄ | |

TABLE 2-continued
The compounds of the formula:
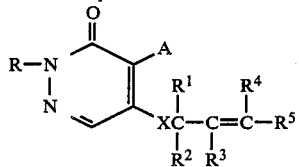
| Comp. No. | R | A | X | R¹ | R² | R³ | R⁴ | R⁵ | M.P. (°C.) |
|---|---|---|---|---|---|---|---|---|---|
| 361 | t-Bu | Cl | O | H | H | H | H | 2-OPro-C₆H₄ | |
| 362 | t-Bu | Cl | O | H | H | Me | H | 4-OPro-C₆H₄ | 129.4~132.7 |
| 363 | t-Bu | Cl | S | H | H | Me | H | 4-OPro-C₆H₄ | 111.8~116.7 |
| 364 | t-Bu | Cl | S | H | H | H | H | 2-Oi-Pro-C₆H₄ | |
| 365 | t-Bu | Cl | S | H | H | Me | H | 4-Oi-Pro-C₆H₄ | |
| 366 | i-Pro | Cl | O | H | H | Me | H | 4-i-Pro-C₆H₄ | |
| 367 | i-Pro | Cl | S | H | H | Me | H | 4-i-Pro-C₆H₄ | |
| 368 | t-Bu | Cl | S | H | H | H | H | 4-i-Pro-C₆H₄ | |
| 369 | t-Bu | Cl | O | H | H | H | H | 4-i-Pro-C₆H₄ | |
| 370 | t-Bu | Cl | S | H | H | Me | H | 4-i-Pro-C₆H₄ | |
| 371 | t-Bu | Cl | S | Me | H | Me | H | 4-i-Pro-C₆H₄ | |

TABLE 2-continued

The compounds of the formula:

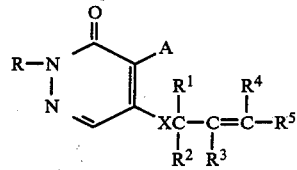

| Comp. No. | R | A | X | R¹ | R² | R³ | R⁴ | R⁵ | M.P. (°C.) |
|---|---|---|---|---|---|---|---|---|---|
| 372 | t-Bu | Cl | S | H | H | H | H | ―C₆H₄―O―Bu (4-) | |
| 373 | t-Bu | Cl | S | H | H | H | H | ―C₆H₄―Bu (2-) | Oil |
| 374 | t-Bu | Cl | S | H | H | H | H | ―C₆H₄―Bu (4-) | Oil, 4-position 70%, 2-position 30% |
| 375 | t-Bu | Cl | O | H | H | H | H | ―C₆H₄―Bu (4-) | Oil, 4-position 70%, 2-position 30% |
| 376 | t-Bu | Cl | O | H | H | H | H | ―C₆H₄―O―i-Bu (4-) | |
| 377 | t-Bu | Cl | O | H | H | H | H | ―C₆H₄―O―s-Bu (4-) | |
| 378 | Et | Cl | O | H | H | H | H | ―C₆H₄―t-Bu (4-) | |
| 379 | Et | Cl | S | H | H | H | H | ―C₆H₄―t-Bu (4-) | |
| 380 | i-Bu | Cl | S | H | H | H | H | ―C₆H₄―t-Bu (4-) | |
| 381 | s-Bu | Cl | S | H | H | H | H | ―C₆H₄―t-Bu (4-) | |
| 382 | t-Bu | Cl | S | H | H | H | H | ―C₆H₄―t-Bu (4-) | 120.0~123.0 |

TABLE 2-continued
The compounds of the formula:
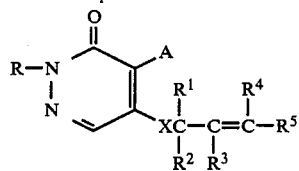
| Comp. No. | R | A | X | R¹ | R² | R³ | R⁴ | R⁵ | M.P. (°C.) |
|---|---|---|---|---|---|---|---|---|---|
| 383 | t-Bu | Cl | O | H | H | H | H | ⟨C₆H₄⟩-t-Bu | 100.0~101.0 |
| 384 | t-Bu | Cl | S | Me | H | H | H | ⟨C₆H₄⟩-t-Bu | 134.8~140.9 |
| 385 | t-Bu | Cl | S | Et | H | H | H | ⟨C₆H₄⟩-t-Bu | |
| 386 | t-Bu | Cl | O | i-Pro | H | H | H | ⟨C₆H₄⟩-t-Bu | |
| 387 | t-Bu | Cl | O | n-Pro | H | H | H | ⟨C₆H₄⟩-t-Bu | |
| 388 | t-Bu | Cl | O | H | H | Me | H | ⟨C₆H₄⟩-t-Bu | 141.7~142.5 |
| 389 | t-Bu | Cl | S | H | H | Me | H | ⟨C₆H₄⟩-t-Bu | |
| 390 | t-Bu | Br | O | H | H | Me | H | ⟨C₆H₄⟩-t-Bu | |
| 391 | t-Bu | Br | S | H | H | Me | H | ⟨C₆H₄⟩-t-Bu | |
| 392 | t-Bu | Cl | O | Me | H | Me | H | ⟨C₆H₄⟩-t-Bu | |
| 393 | t-Bu | Cl | S | Me | H | Me | H | ⟨C₆H₄⟩-t-Bu | |

TABLE 2-continued
The compounds of the formula:
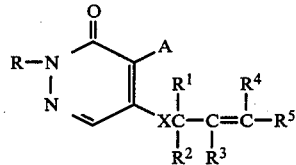
| Comp. No. | R | A | X | R¹ | R² | R³ | R⁴ | R⁵ | M.P. (°C.) |
|---|---|---|---|---|---|---|---|---|---|
| 394 | t-Bu | Cl | S | H | H | Et | H | —C₆H₄—t-Bu | 103.5~106.8 |
| 395 | t-Bu | Cl | O | H | H | Et | H | —C₆H₄—t-Bu | 143.8~148.5 |
| 396 | t-Bu | Cl | S | H | H | Pro | H | —C₆H₄—t-Bu | Oil |
| 397 | t-Bu | Cl | S | H | H | i-Pro | H | —C₆H₄—t-Bu | |
| 398 | t-Bu | Cl | S | H | H | H | Me | —C₆H₄—t-Bu | Oil |
| 399 | t-Bu | Cl | O | H | H | H | Me | —C₆H₄—t-Bu | Oil |
| 400 | t-Bu | Cl | S | H | H | H | Et | —C₆H₄—t-Bu | |
| 401 | t-Bu | Cl | S | H | H | H | Pro | —C₆H₄—t-Bu | |
| 402 | t-Pen | Cl | S | H | H | H | H | —C₆H₄—t-Bu | |
| 403 | t-Pen | Cl | O | H | H | H | H | —C₆H₄—t-Bu | |
| 404 | Hex | Cl | S | H | H | H | H | —C₆H₄—t-Bu | |

TABLE 2-continued
The compounds of the formula:
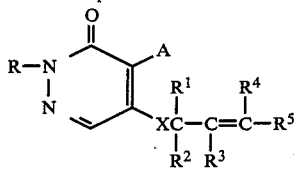
| Comp. No. | R | A | X | R¹ | R² | R³ | R⁴ | R⁵ | M.P. (° C.) |
|---|---|---|---|---|---|---|---|---|---|
| 405 | Hex | Cl | O | H | H | H | H | —C₆H₄—t-Bu (p) | |
| 406 | t-Bu | Cl | O | H | H | H | H | —C₆H₄—t-Pen (p) | |
| 407 | t-Bu | Cl | S | H | H | H | H | —C₆H₄—t-Pen (p) | |
| 408 | t-Bu | Cl | S | H | H | H | H | —C₆H₄—Hex (p) | |
| 409 | t-Bu | Cl | S | H | H | H | H | —C₆H₃(CH₃)—Pen | |
| 410 | Et | Cl | S | H | H | H | H | —C₆H₄—cyclopropyl | |
| 411 | t-Bu | Cl | S | H | H | H | H | —C₆H₄—cyclopropyl | |
| 412 | t-Bu | Cl | O | H | H | Me | H | —C₆H₄—cyclopropyl | |
| 413 | t-Bu | Cl | S | H | H | Me | H | —C₆H₄—cyclopropyl | |
| 414 | t-Bu | Cl | O | H | H | H | H | —C₆H₄—cyclohexyl | |
| 415 | t-Bu | Cl | O | H | H | H | H | —C₆H₄—O—Pen | |

TABLE 2-continued
The compounds of the formula:
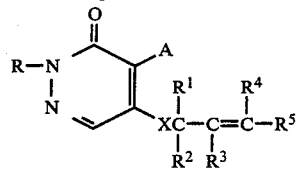
| Comp. No. | R | A | X | R¹ | R² | R³ | R⁴ | R⁵ | M.P. (° C.) |
|---|---|---|---|---|---|---|---|---|---|
| 416 | t-Bu | Cl | O | H | H | H | H | | |
| 417 | t-Bu | Cl | O | H | H | H | H | | |
| 418 | Et | Cl | S | H | H | H | H | | |
| 419 | Pro | Cl | S | H | H | H | H | | |
| 420 | t-Bu | Cl | S | H | H | H | H | | |
| 421 | t-Bu | Cl | O | H | H | Me | H | | |
| 422 | t-Bu | Cl | S | H | H | Me | H | | |
| 423 | t-Bu | Cl | S | Me | H | Me | H | | |
| 424 | t-Bu | Cl | O | Me | H | Me | H | | |
| 425 | t-Bu | Br | S | H | H | Me | H | | |
| 426 | t-Bu | Cl | O | H | H | H | H | | |

TABLE 2-continued
The compounds of the formula:
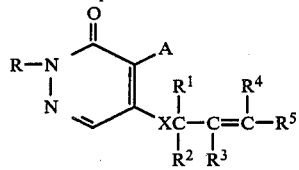
| Comp. No. | R | A | X | R¹ | R² | R³ | R⁴ | R⁵ | M.P. (°C.) |
|---|---|---|---|---|---|---|---|---|---|
| 427 | t-Bu | Cl | O | H | H | H | H | —C₆H₄—SO₂CH₃ (p) | |
| 428 | t-Bu | Cl | S | H | H | H | H | —C₆H₄—S—i-Pro (p) | |
| 429 | t-Bu | Cl | S | H | H | H | H | —C₆H₄—S—Bu (p) | |
| 430 | Et | Cl | S | H | H | H | H | 2-CF₃-C₆H₄— | |
| 431 | Et | Br | S | H | H | H | H | 2-CF₃-C₆H₄— | |
| 432 | t-Bu | Cl | S | H | H | H | H | 2-CF₃-C₆H₄— | |
| 433 | t-Bu | Cl | O | H | H | Me | H | 2-CF₃-C₆H₄— | |
| 434 | t-Bu | Cl | S | H | H | Me | H | 2-CF₃-C₆H₄— | |
| 435 | t-Bu | Br | S | H | H | Me | H | 2-CF₃-C₆H₄— | |
| 436 | t-Bu | Cl | S | H | H | H | H | 3-CF₃-C₆H₄— | |

TABLE 2-continued
The compounds of the formula:
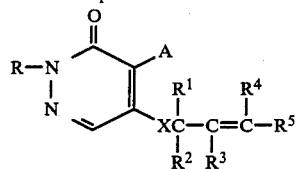
| Comp. No. | R | A | X | R¹ | R² | R³ | R⁴ | R⁵ | M.P. (°C.) |
|---|---|---|---|---|---|---|---|---|---|
| 437 | t-Bu | Cl | O | H | H | H | H | 3-CF₃-C₆H₄ | |
| 438 | Et | Cl | S | H | H | Me | H | 4-CF₃-C₆H₄ | |
| 439 | Et | Cl | O | H | H | Me | H | 4-CF₃-C₆H₄ | |
| 440 | i-Pro | Cl | S | H | H | Me | H | 4-CF₃-C₆H₄ | |
| 441 | i-Pro | Cl | O | H | H | Me | H | 4-CF₃-C₆H₄ | |
| 442 | t-Bu | Cl | S | H | H | H | H | 4-CF₃-C₆H₄ | 75.0~77.0 |
| 443 | t-Bu | Cl | O | H | H | H | H | 4-CF₃-C₆H₄ | |
| 444 | t-Bu | Cl | S | H | H | Me | H | 4-CF₃-C₆H₄ | |
| 445 | t-Bu | Cl | O | H | H | Me | H | 4-CF₃-C₆H₄ | |
| 446 | t-Bu | Cl | S | Me | H | Me | H | 4-CF₃-C₆H₄ | |
| 447 | t-Bu | Cl | S | H | H | Et | H | 4-CF₃-C₆H₄ | |

TABLE 2-continued

The compounds of the formula:

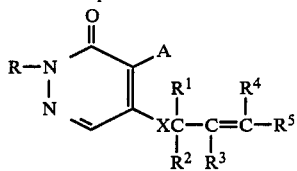

| Comp. No. | R | A | X | $R^1$ | $R^2$ | $R^3$ | $R^4$ | $R^5$ | M.P. (° C.) |
|---|---|---|---|---|---|---|---|---|---|
| 448 | t-Bu | Cl | S | H | H | i-Pro | H | 4-CF$_3$-C$_6$H$_4$ | |
| 449 | t-Bu | Cl | S | H | H | H | H | 4-OCHF$_2$-C$_6$H$_4$ | |
| 450 | t-Bu | Cl | O | H | H | H | H | 4-OCHF$_2$-C$_6$H$_4$ | |
| 451 | t-Bu | Cl | S | H | H | H | H | 4-OCH$_2$CF$_3$-C$_6$H$_4$ | |
| 452 | t-Bu | Cl | O | H | H | H | H | 4-OCH$_2$CF$_3$-C$_6$H$_4$ | |
| 453 | t-Bu | Cl | O | H | H | H | H | 4-SCF$_3$-C$_6$H$_4$ | |
| 454 | t-Bu | Cl | O | H | H | H | H | 4-SCHF$_2$-C$_6$H$_4$ | |
| 455 | t-Bu | Cl | S | H | H | H | H | 4-OCH$_2$CH=CH$_2$-C$_6$H$_4$ | |
| 456 | t-Bu | Cl | O | H | H | H | H | 4-OCH$_2$CH=CH$_2$-C$_6$H$_4$ | |
| 457 | t-Bu | Cl | O | H | H | H | H | 4-N(CH$_3$)$_2$-C$_6$H$_4$ | |
| 458 | t-Bu | Cl | S | H | H | Me | H | 4-Si(CH$_3$)$_3$-C$_6$H$_4$ | |

TABLE 2-continued
The compounds of the formula:
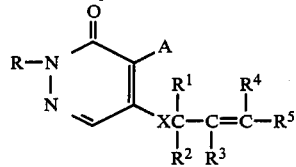
| Comp. No. | R | A | X | R¹ | R² | R³ | R⁴ | R⁵ | M.P. (° C.) |
|---|---|---|---|---|---|---|---|---|---|
| 459 | t-Bu | Cl | O | H | H | Me | H | —C₆H₄—Si(CH₃)₃ | |
| 460 | t-Bu | Cl | S | H | H | H | H | 2-NO₂-C₆H₄— | |
| 461 | t-Bu | Cl | O | H | H | H | H | 2-NO₂-C₆H₄— | |
| 462 | t-Bu | Cl | S | H | H | H | H | 4-NO₂-C₆H₄— | |
| 463 | t-Bu | Cl | S | Me | H | H | H | 4-biphenyl | 126.0~129.5 |
| 464 | t-Bu | Cl | O | H | H | Me | H | 4-biphenyl | 142.5~152.6 |
| 465 | t-Bu | Cl | O | H | H | H | H | 4'-Cl-biphenyl-4-yl | |
| 466 | t-Bu | Cl | O | H | H | H | H | 2',4'-Cl₂-biphenyl-4-yl | |
| 467 | t-Bu | Cl | S | H | H | H | H | 2'-CH₃-biphenyl-4-yl | |
| 468 | t-Bu | Cl | O | H | H | H | H | 4-(4-CF₃-phenoxy)phenyl | |
| 469 | t-Bu | Cl | S | H | H | H | H | 4-(4-CF₃-phenoxy)phenyl | |

TABLE 2-continued

The compounds of the formula:

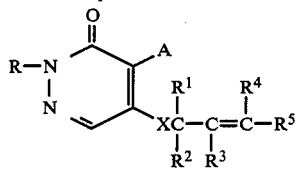

| Comp. No. | R | A | X | R¹ | R² | R³ | R⁴ | R⁵ | M.P. (° C.) |
|---|---|---|---|---|---|---|---|---|---|
| 470 | t-Bu | Cl | O | H | H | H | H | 4-(2-Cl-4-CF₃-phenoxy)phenyl | |
| 471 | t-Bu | Cl | O | H | H | H | H | 4-(benzyloxy)phenyl | |
| 472 | t-Bu | Cl | S | H | H | H | H | 4-(benzyloxy)phenyl | |
| 473 | t-Bu | Cl | S | H | H | H | H | 4-(2-F-benzyloxy)phenyl | |
| 474 | t-Bu | Cl | O | H | H | H | H | 4-(2-F-benzyloxy)phenyl | |
| 475 | t-Bu | Cl | O | H | H | H | H | 4-(4-NO₂-benzyloxy)phenyl | |
| 476 | t-Bu | Cl | S | H | H | H | H | 4-(4-NO₂-benzyloxy)phenyl | |
| 477 | t-Bu | Cl | S | H | H | H | H | 4-(4-OCH₃-benzyloxy)phenyl | |
| 478 | t-Bu | Cl | O | H | H | H | H | 4-(4-OCH₃-benzyloxy)phenyl | |
| 479 | t-Bu | Cl | O | H | H | Me | H | 4-(3-Cl-benzyloxy)phenyl | |

TABLE 2-continued

The compounds of the formula:

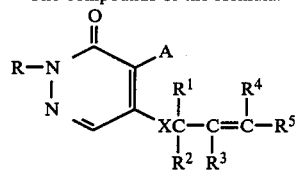

| Comp. No. | R | A | X | R¹ | R² | R³ | R⁴ | R⁵ | M.P. (° C.) |
|---|---|---|---|---|---|---|---|---|---|
| 480 | t-Bu | Cl | S | H | H | Me | H | 4-(3-chlorobenzyloxy)phenyl | |
| 481 | t-Bu | Cl | O | H | H | Me | H | 4-(2-methylbenzyloxy)phenyl | |
| 482 | t-Bu | Cl | S | H | H | Me | H | 4-(2-methylbenzyloxy)phenyl | |
| 483 | t-Bu | Cl | S | H | H | H | H | 4-benzoylphenyl | |
| 484 | t-Bu | Cl | O | H | H | Me | H | 4-(4-chlorobenzoyl)phenyl | |
| 485 | t-Bu | Cl | S | H | H | Me | H | 4-(4-chlorobenzoyl)phenyl | |
| 515 | t-Bu | Cl | S | H | H | Cl | H | Cl | Oil |
| 516 | Et | Cl | S | H | H | Me | H | 4-OPro-phenyl | 83.8~84.4 |
| 517 | t-Bu | Cl | S | H | H | Me | H | 3-methyl-4-pentylphenyl | |
| 518 | t-Bu | Cl | S | H | H | H | H | 2-ethyl-4-butylphenyl | |
| 519 | t-Bu | Cl | S | H | H | H | H | 3-methyl-4-propylphenyl | |

TABLE 2-continued
The compounds of the formula:
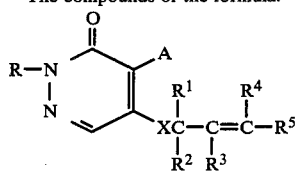
| Comp. No. | R | A | X | R¹ | R² | R³ | R⁴ | R⁵ | M.P. (° C.) |
|---|---|---|---|---|---|---|---|---|---|
| 520 | t-Bu | Cl | S | H | H | H | H | ![Pro, Pen-phenyl] | |
| 521 | t-Bu | Cl | O | H | H | Pro | H | ![p-t-Bu-phenyl] | 123.1~124.6 |
| 522 | t-Bu | Cl | S | H | H | H | H | ![p-C₂H₅-phenyl] | 77.9~79.2 |
| 523 | t-Bu | Cl | S | H | H | H | H | ![CH₃, OBu-phenyl] | |
| 524 | t-Bu | Cl | S | H | H | H | H | ![CH₃, Oi-Pro-phenyl] | |
| 525 | t-Bu | Cl | S | H | H | H | H | ![CH₃, i-Pro-phenyl] | |
| 526 | t-Bu | Cl | S | H | H | H | H | ![p-Pro-phenyl] | |
| 527 | t-Bu | Cl | S | H | H | Me | H | ![p-Pro-phenyl] | |
| 528 | t-Bu | Cl | O | H | H | Me | H | ![CH₃, CH₃-phenyl] | |
| 529 | t-Bu | Cl | O | H | H | H | H | ![p-C₂H₅-phenyl] | 121.9~123.1 |

TABLE 2-continued
The compounds of the formula:
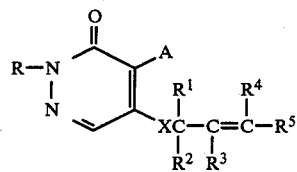
| Comp. No. | R | A | X | R¹ | R² | R³ | R⁴ | R⁵ | M.P. (°C.) |
|---|---|---|---|---|---|---|---|---|---|
| 530 | t-Bu | Cl | O | H | H | Me | H | 4-Br-C₆H₄ | 91.0~92.5 |
| 531 | t-Bu | Cl | S | H | H | H | H | 2,4,6-tri-Me-C₆H₂ | 93.0~95.0 |
| 532 | t-Bu | Cl | O | H | H | H | H | 2,4,6-tri-Me-C₆H₂ | |
| 533 | t-Bu | Cl | S | H | H | H | H | 2-Cl-4-t-Bu-C₆H₃ | |
| 534 | t-Bu | Cl | S | H | H | Me | H | 2-Cl-4-t-Bu-C₆H₃ | |
| 535 | t-Bu | Cl | S | H | H | H | H | 2-Me-4-t-Bu-C₆H₃ | |
| 536 | t-Bu | Cl | S | H | H | Me | H | 2-Me-4-t-Bu-C₆H₃ | |
| 537 | t-Bu | Cl | S | H | H | H | H | 2-Br-4-t-Bu-C₆H₃ | |

TABLE 2-continued
The compounds of the formula:
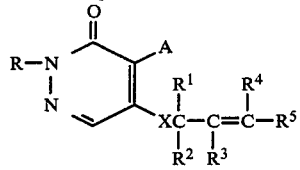
| Comp. No. | R | A | X | R¹ | R² | R³ | R⁴ | R⁵ | M.P. (° C.) |
|---|---|---|---|---|---|---|---|---|---|
| 538 | t-Bu | Cl | S | H | H | Me | H | 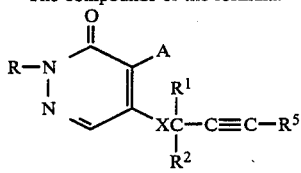 | |
TABLE 3
The compounds of the formula:
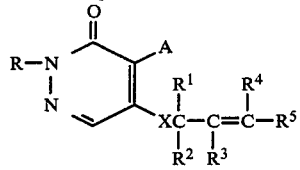
| Comp. No. | R | A | X | R¹ | R² | R⁵ | M.P. (°C.) |
|---|---|---|---|---|---|---|---|
| 486 | Et | Cl | O | H | H | Me | |
| 487 | i-Pro | Cl | O | H | H | Me | |
| 488 | t-Bu | Cl | O | H | H | Me | |
| 489 | t-Bu | Br | O | H | H | Me | |
| 490 | t-Bu | Cl | S | H | H | Et | |
| 491 | t-Bu | Cl | O | H | H | Et | |
| 492 | t-Bu | Cl | S | H | H | Pro | |
| 493 | t-Bu | Cl | O | H | H | Pro | |
| 494 | t-Bu | Cl | O | H | H | 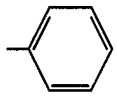 | 142.5~146.5 |
| 495 | t-Bu | Cl | S | H | H | 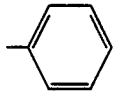 | |
| 496 | t-Bu | Cl | O | H | H | 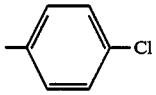 | |
| 497 | t-Bu | Cl | S | H | H | 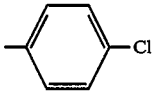 | |
| 498 | t-Bu | Cl | O | H | H | 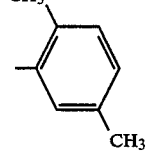 | |

TABLE 3-continued
The compounds of the formula:
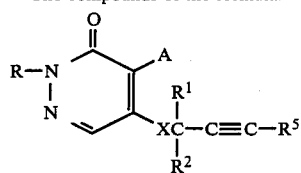
| Comp. No. | R | A | X | R¹ | R² | R⁵ | M.P. (°C.) |
|---|---|---|---|---|---|---|---|
| 499 | t-Bu | Cl | S | H | H | 2,4-dimethylphenyl | |
| 500 | t-Bu | Cl | O | H | H | 4-CF₃-phenyl | |
| 501 | t-Bu | Cl | S | H | H | 4-CF₃-phenyl | |
| 502 | t-Bu | Cl | O | H | H | 4-t-Bu-phenyl | |
| 503 | t-Bu | Cl | S | H | H | 4-t-Bu-phenyl | |
| 504 | t-Bu | Br | O | H | H | 4-t-Bu-phenyl | |
| 505 | t-Bu | Br | S | H | H | 4-t-Bu-phenyl | |
| 506 | t-Bu | Cl | O | H | H | 4-OCH₃-phenyl | |
| 507 | t-Bu | Cl | S | H | H | 4-OCH₃-phenyl | |
| 508 | t-Bu | Cl | O | H | H | 2,4-difluorophenyl | |

TABLE 3-continued

The compounds of the formula:

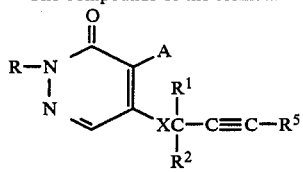

| Comp. No. | R | A | X | R¹ | R² | R⁵ | M.P. (°C.) |
|---|---|---|---|---|---|---|---|
| 509 | t-Bu | Cl | S | H | H | 2,4-difluorophenyl | |
| 510 | t-Bu | Br | O | H | H | 2,4-difluorophenyl | |
| 511 | t-Bu | Cl | O | H | H | 4-biphenyl | |
| 512 | t-Bu | Cl | S | H | H | 4-biphenyl | |
| 513 | t-Bu | Cl | O | H | H | 4-(4-trifluoromethylphenoxy)phenyl | |
| 514 | t-Bu | Cl | S | H | H | 4-(4-trifluoromethylphenoxy)phenyl | |

The compound of the formula (VI-a):

(VI-a)

(wherein, A' and R denote a straight or branched $C_1$ to $C_6$ alkyl and X' is as defined previously in formula (VI)) which are used as a starting material in the process of the invention can be prepared by reacting a Grignard reagent such as a straight or branched $C_1$ to $C_6$ alkyl magnesium iodide with a compound of the formula (VIII):

(VIII)

(wherein, R is as defined in formula (I)) in a solvent having a relatively low polarity such as toluene to produce a compound of the formula (VI-b):

(VI-b)

(wherein, A' and R are as defined in formula (VI-a)), and then converting the compound of the formula (VI-b) into the derivatives thereof via various chemical reactions, for example, as follows:

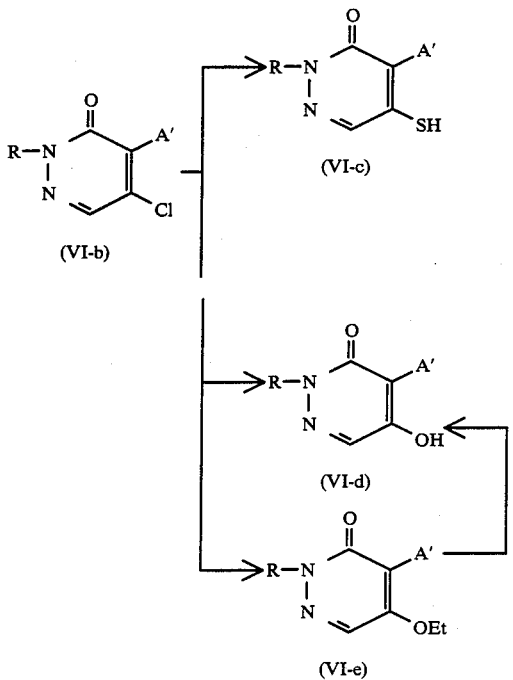

Then the compound of the formula (VI):

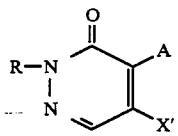

is reacted with the formula (VII):

$$X''\text{—}Q \qquad \text{(VII)}$$

(wherein, Q, R, A, X' and X" are as defined above in formulae (I), (VI) and (VII)).

The reaction of the compound of the formula (VI) with the compound of the formula (VII) is usually effected in solvent such as acid amides (e.g. N,N-dimethylformamide, hexamethyl phosphoric amide), alcohols (e.g. methanol, ethanol, cinnamyl alcohol), tetrahydrofuran, acetonitrile, and preferably in N,N-dimethylformamide.

The reaction temperature is usually in the range of room temperature to 150° C., preferably 15° to 120° C.

Preparation of the compounds of the invention and the starting materials thereof is described in detail by way of the examples and reference examples which are not to restrict the invention.

REFERENCE EXAMPLE 1

Synthesis of 2-tert.-butyl-5-chloro-4-methyl-3(2H)-pyridazinone (starting material)

To a solution of 6.0 g (0.25 mol) of magnesium in 50 ml of dry tetrahydrofuran was added dropwise 35.5 g (0.25 mol) of methyl iodide under stream of nitrogen to produce a Grignard reagent. After completion of adding the methyl iodide, 1000 ml of dry toluene was added thereto. The resulting solution was heated to 60° to 70° C. and added dropwise with methyl iodide until the magnesium was completely consumed.

The resulting Grignard reagent was cooled to room temperature and was added dropwise over 20 minutes with 22.1 g (0.1 mol) of 2-tert.-butyl-4,5-dichloro-3(2H)-pyridazinone dissolved in 200 ml of dry toluene. After completion of adding, the reaction liquid was subjected to reaction for 1.5 hours at room temperature and then poured into a solution of 100 ml of conc. hydrochloric acid in 900 ml of ice-water to effect extraction. The resulting organic layer was then washed with 500 ml of 10% aqueous solution of sodium hydroxide and then with 500 ml of water, and dried over anhydrous sodium sulfate. The solvent was distilled off under reduced pressure to give 17.2 g of a crude product. The crude product was subjected to distillation (boiling point: 60° to 62° C./0.22 mmHg) and then column chromatography (silica gel; hexane:acetone=15:1) for separation and purification to give 4.5 g of 2-tert.-butyl-5-chloro-4-methyl-3(2H)-pyridazinone.

$N_D^{20} = 1.5238$.

NMR (CDCl$_3$, δ, TMS): 1.63 (9H, s), 2.23 (3H, s), 7.66 (1H, s).

REFERENCE EXAMPLE 2

Synthesis of 2-tert.-butyl-5-mercapto-4-methyl-3(2H)-pyridazinone (starting material)

To 75ml of ethanol were added 17.0 g (0.085 mol) of 2-tert.-butyl-5-chloro-4-methyl-3(2H)-pyridazinone and 8.5 g (0.106 mol) of 70% sodium hydrosulfide, and the mixture was stirred under reflux for 4 hours. After cooling, the mixture was poured into 300 ml of ice-water and extracted with 200 ml of ethyl ether. The ether layer was washed with 100 ml of water and dried over anhydrous sodium sulfate. The solvent was then distilled off therefrom to give 16.3 g of a crude product.

NMR (CDCl$_3$, δ, TMS): 1.61 (9H, s), 2.23 (3H, s), 7.46 (1H, s).

M/Z: 198 (P+), 143 (BP).

The compound thus obtained was used in the following synthesis example as a starting material without subjecting to purification. Incidentally, this compound was identified by converting it to the following two derivatives.

(a) 2-tert.-butyl-4-methyl-5-methylthio-3(2H)-pyridazinone

The crude product 2.0 g (0.01 mol) of 2-tert.-butyl-5-mercapto-4-methyl-3(2H)-pyridazinone as synthesized in the above and 1.4 g (0.01 mol) of methyl iodide were dissolved in 20 ml of dimethylformamide and then added with 2.0 g of sodium carbonate with stirring at room temperature. The reaction liquid was stirred for 3 hours at 70° C. After allowing to cool the reaction liquid was poured into 200 ml of water and extracted with 50 ml of benzene. The benzene layer was washed successively with 50 ml of 10% sodium hydroxide, 50 ml of 1N hydrochloric acid and 100 ml of water, dried over anhydrous sodium sulfate and freed of solvent by distillation to give 2.0 g of a crude product. The crude product was recrystallized from 20 ml of isopropyl ether to give 1.4 g of 2-tert.-butyl-4-methyl-5-methylthio-3(2H)-pyridazinone.

M.P.: 115.0°~116.0° C.

NMR (CDCl$_3$, δ, TMS): 1.61 (9H, s), 2.11 (3H, s), 2.48 (3H, s), 7.55 (1H, s).

(b) 2-tert.-butyl-4-methyl-5-(2',4'-dinitrophenylthio)-3(2H)-pyridazinone

To a solution of 2.0 g (0.01 mol) of the crude product of 2-tert.-butyl-5-mercapto-4-methyl-3(2H)-pyridazinone dissolved in 15 ml of ethanol was added 1.5 ml of 20% sodium hydroxide under stirring at room temperature. After stirring for additional 15 minutes at room temperature, the resulting mixture was added dropwise with a solution of 1.4 g of 2,4-dinitrofluorobenzene dissolved in 5 ml of ethanol and stirred for 10 minutes at room temperature. Crystalline precipitates were collected by filtration, washed with 50 ml of water and 50 ml of ethanol and then recrystallized from 50 ml of benzene to give 2.0 g of 2-tert.-butyl-4-methyl-5-(2',4'-dinitrophenylthio)-3(2H)-pyridazinone.

M.P.: 185.5°~187.5° C.

NMR (CDCl$_3$, δ, TMS): 1.67 (9H, s), 2.32 (3H, s), 7.18 (1H, d, J=9 Hz), 7.58 (1H, s), 8.30 (1H, dd, J=9 2 Hz), 9.06 (1H, d, J=2 Hz).

REFERENCE EXAMPLE 3

Synthesis of 2-tert.-butyl-5-hydroxy-4-methyl-3(2H)-pyridazinone (starting material)

(Method A): A mixture of 2.0 g (0.01 mol) of 2-tert.-butyl-5-chloro-4-methyl-3(2H)-pyridazinone and 2.8 g (0.05 mol) of potassium hydroxide was added to 30 ml of ethylene glycol and stirred at 130° C. for 4 hours. After allowing to cool, the reaction liquid was poured into 200 ml of water and added with 20 ml of 6N hydrochloric acid. The crystals thus precipitated were collected by filtration. After drying, the crystals were washed with 30 ml of hot isopropyl ether to give 1.7 g of 2-tert.-butyl-5-hydroxy-4-methyl-3(2H)-pyridazinone.

M.P.: 236.0°~239.0° C.

NMR (CDCl$_3$, δ, TMS): 1.62 (9H, s), 1.97 (3H, s), 4.63 (1H, s), 7.60 (1H, s).

M/Z: 182 (P+), 127 (BP).

(Method B): In a mixture of 25 ml of ethanol and 25 ml of water was dissolved 4.7 g of potassium hydroxide and the 5.0 g (0.025 mol) of 2-tert.-butyl-5-chloro-4-methyl-3(2H)-pyridazinone was added thereto. The resulting mixture was stirred under reflux for 26 hours. After ethanol was distilled off, the reaction mixture was added with 100 ml of water and extracted with 100 ml of chloroform. The chloroform layer was washed with 100 ml of water, dried over anhydrous sodium sulfate and free of solvent by distillation to give 5.2 g of a crude product. The crude product was recrystallized from 30 ml of hexane to give 4.5 g of 2-tert.-butyl-5-ethoxy-4-methyl-3(2H)-pyridazinone.

M.P.: 70.0°~71.5° C.

NMR (CDCl$_3$, δ, TMS): 1.40 (3H, t, J=7 Hz), 2.00 (3H, s), 1.61 (9H, s), 4.14 (2H, q, J=7 Hz), 7.65 (1H, s).

The resulting 2-tert.-butyl-5-ethoxy-4-methyl-3(2H)-pyridazinone (1.7 g) and potassium hydroxide (6.0 g) were added to 30 ml of ethyleneglycol, and the mixture was stirred under reflux for 3 hours. The reaction mixture was poured into 200 ml of water and added with 30 ml of 6N-hydrochloric acid. The crystals thus precipitated was collected by filtration. After drying, the crystals were washed with hot hexane to give 1.3 g of 2-tert.-butyl-5-hydroxy-4-methyl-3(2H)-pyridazinone.

The melting point and the result of NMR analysis of this product were identical with those of the product obtained by the Method A.

REFERENCE EXAMPLE 4

Synthesis of 2-tert.-butyl-5-chloro-4-ethyl-3(2H)-pyridazinone (starting material)

To a mixed solution of 43 g of ethyl magnesium bromide (a solution containing 3 mol per liter of ether) and 200 ml of dry toluene was added 22.1 g (0.1 mol) of 2-tert.-butyl-5-dichloro-3(2H)-pyridazinone divided into three portions under a stream of nitrogen at room temperature while throughly stirring the mixed solution. The temperature of the reaction mixture rose to approximately 60° c: but stirring was continued for about 30 minutes. About 300 ml of cold water was added thereto, and the resulting mixture was stirred vigorously and then transferred into a separatory funnel. The aqueous layer was discarded, and the organic layer was washed with about 200 ml of water and then dried over anhydrous sodium sulfate. The solvent was distilled off therefrom to obtain a pale brown oily substance. The substance was subjected to separation and purification by means of column chromatography (silica gel; using benzene as an eluent) to give 14.5 g of pale yellow crystals.

M.P.: 61.5°~62.5° C.

NMR (CDCl$_3$, δ, TMS): 1.14 (3H, t, J=7 Hz), 1.61 (9H, s), 2.72 (2H, q, J=7 Hz), 7.62 (1H, s).

REFERENCE EXAMPLE 5

In accordance with the procedure in Reference Example 4, the starting materials shown in Table 4 were obtained.

TABLE 4

The compounds of the formula:

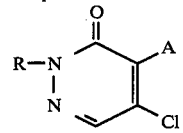

| R | A | M.P. (°C.) | NMR (CDCl$_3$, δ, TMS) |
|---|---|---|---|
| t-Bu | Pro | Oil | 1.98 (3H, t, J = 7Hz) |
| | | | 1.62 (9H, s), 1.68 (2H, m) |
| | | | 2.70 (2H, t, J = 7Hz) |
| | | | 7.64 (1H, s) |
| Et | Me | 54.0~57.0 | 1.35 (3H, t, J = 7Hz) |
| | | | 2.25 (3H, s) |
| | | | 4.16 (2H, q, J = 7Hz) |
| | | | 7.68 (1H, s) |
| Et | Et | Oil | 1.16 (3H, t, J = 7Hz) |
| | | | 1.35 (3H, t, J = 7Hz) |
| | | | 2.75 (2H, q, J = 7Hz) |
| | | | 4.18 (2H, q, J = 7Hz) |
| | | | 7.68 (1H, s) |

SYNTHESIS EXAMPLE 1:

Synthesis of 2-t-butyl-4-methyl-5-(p-phenylbenzylthio)-3(2H)-pyridazinone (Compound No. 49)

To 10 ml of dry N,N-dimethylformamide was added 0.75 g of 55% sodium hydride. The resulting mixture was kept at 0° C. and added dropwise with a solution of 3.2 g of p-phenylbenzyl mercaptan dissolved in 15 ml of N,N-dimethylformamide. After ten minutes passed, the resulting mixture was added dropwise with a solution of 3.2 g of 2-t-butyl-5-chloro-4-methyl-3(2H)-pyridazinone dissolved in 15 ml of N,N-dimethylformamide.

After completion of dropwise addition, the resulting mixture was reacted at 80° C. for one hour. The resulting solution was poured into 50 ml of water and extracted twice with 50 ml of diethyl ether. The resulting organic layer was dried over anhydrous sodium sulfate, and freed of solvent by distillation under reduced pressure to give 4.8 g of crude product. The crude product was recrystallized from 5 ml of hexane to obtain 2.6 g of 2-t-butyl-4-methyl-5-(p-phenyl-benzylthio)-3(2H)-pyridazinone.

M.P.: 112.0°~115.0° C.

NMR (CDCl$_3$, δ, TMS): 1.62 (9H, s), 2.17 (3H, s), 4.19 (2H, s), 7.30~7.60 (9H, s), 7.64 (1H, s).

SYNTHESIS EXAMPLE 2:

Synthesis of 2-t-butyl-4-methyl-5-(p-propoxybenzylthio)-3(2H)-pyridazinone (Compound No. 91)

To 5 ml of dry N,N-dimethylformamide was added 0.24 g of 55% sodium hydride. The resulting mixture was kept at 0° C. and added dropwise with a solution of 0.91 g of p-propoxybenzyl mercaptan dissolved in 5 ml of N,N-dimethylformamide. After ten minutes passed, the resulting mixture was added dropwise with a solution of 1.0 g of 2-t-butyl-5-chloro-4-methyl-3(2H)-pyridazinone dissolved in 5 ml of N,N-dimethylformamide. After completion of dropwise addition, the resulting mixture was reacted at room temperature for four hours. The resulting solution was poured into 50 ml of water and extracted twice with 50 ml of diethyl ether. The resulting organic layer was dried over anhydrous sodium sulfate, and freed of solvent by distillation under reduced pressure to give 1.7 g of crude product. The crude product was fractionated on thin layer chromatography to obtain 0.8 g of 2-t-butyl-4-methyl-5-(p-propoxybenzylthio)-3(2H)-pyridazinone.

$N_D^{20.0} = 1.5810$.

NMR (CDCl$_3$, δ, TMS): 1.01 (3H, t, J=7 Hz), 1.60 (9H, s), 2.12 (3H, s), 1.60~2.30 (2H, m), 3.88 (2H, t, J=6 Hz), 4.10 (2H, s), 6.83 (2H, d, J=8 Hz), 7.23 (2H, d, J=8 Hz), 7.60 (1H, s).

SYNTHESIS EXAMPLE 3:

Synthesis of 2-t-butyl-5-(p-t-butylbenzylthio)-4-methyl-3(2H)-pyridazinone (Compound No. 170)

To 30 ml of dry tetrahydrofuran was added 0.5 g of 55% sodium hydride. The resulting mixture was kept at room temperature and added dropwise with a solution of 1.8 g of p-t-butylbenzyl mercaptan dissolved in 10 ml of tetrahydrofuran. After ten minutes passed, the resulting mixture was added dropwise with a solution of 2.0 g of 2-t-butyl-5-chloro-4-methyl-3(2H)-pyridazinone dissolved in 10 ml of tetrahydrofuran. After completion of dropwise addition, the resulting mixture was reacted for 2 hours under heat-reflux. After the reaction mixture was concentrated under reduced pressure, it was poured into 50 ml of water and extracted twice with 50 ml of diethyl ether. The resulting organic layer was dried over anhydrous sodium sulfate and freed of solvent by distillation under reduced pressure to give 3.5 g of crude product. The crude product was recrystallized from 5 ml of hexane to obtain 1.6 g of 2-t-butyl-5-(p-t-butylbenzylthio)-4-methyl-3(2H)-pyridazinone.

M.P.: 91.0°~92.0° C.

NMR (CDCl$_3$, δ, TMS): 1.30 (9H,s), 1.61 (9H,s), 2.15 (3H, s), 4.16 (2H, s), 7.30 (4H, s), 7.62 (1H, s).

SYNTHESIS EXAMPLE 4:

Synthesis of 2-t-butyl-(α-ethyl-p-t-butylbenzylthio)-4-methyl-3(2H)-pyridazinone (Compound No. 174)

To a solution of 0.8 g (0.004 mol) of 2-t-butyl-5-mercapto-4-methyl-3(2H)-pyridazinone and 0.84 g (0.004 mol) of α-ethyl-p-t-butylbenzyl chloride dissolved in 20 ml of N,N-dimethylformamide was added 1.0 g (0.01 mol) of sodium carbonate at room temperature under stirring. After addition, the resulting mixture was stirred at 70°~80° C. for four hours. After allowed to cool, the reaction mixture was poured into 200 ml of water and then extracted with 100 ml of benzene. The resulting benzene layer was washed with 100 ml of water, dried over anhydrous sodium sulfate, and freed of solvent by distillation to give 1.5 g of crude product. The crude product was fractionated on silica gel column chromatography [developer: a mixed solvent of benzene and ethyl acetate (10:1 mixture)] to obtain 0.8 g of 2-t-butyl-5-(α-ethyl-p-t-butylbenzylthio)-4-methyl-3(2H)-pyridazinone.

$N_D^{20} = 1.5630$.

NMR (CDCl$_3$, δ, TMS): 0.95 (3H, t, J=7 Hz), 1.29 (9H, s), 1.58 (9H, s), 1.70~2.30 (2H, m), 2.14 (3H, s), 4.18 (1H, t, J=7 Hz), 7.26 (4H, s), 7.52 (1H, s).

SYNTHESIS EXAMPLE 5:

Synthesis of 2-t-butyl-5-(p-fluorobenzyloxy)-4-methyl-3(2H)-pyridazinone (Compound No. 3)

To a solution of 0.63 g (0.005 mol) of p-fluorobenzyl alcohol dissolved in 20 ml of N,N-dimethylformamide was added 0.24 g of 55% sodium hydride at room temperature under stirring. After addition, the resulting mixture was further stirred at room temperature for fifteen minutes. The reaction liquid was added dropwise with 1.0 g of 2-t-butyl-5-chloro-4-methyl-3(2H)-pyridazinone, and was stirred at room temperature for eight hours. The reaction mixture was poured into 200 ml of water and then extracted with 50 ml of benzene. The resulting benzene layer was washed successively with 50 ml of 10% sodium hydroxide, 50 ml of 1N-hydrochloric acid, and 100 ml of water, dried over anhydrous sodium sulfate, and freed of solvent by distillation to give 1.5 g of crude product. The crude product was recrystallized from 20 ml of hexane to obtain 0.9 g of 2-t-butyl-5-(p-fluorobenzyloxy)-4-methyl-3(2H)-pyridazinone.

M.P.: 65.0°~66.5° C.

NMR (CDCl$_3$, δ, TMS): 1.62 (9H, s), 2.04 (3H, s), 5.13 (2H, s), 6.85~7.45 (4H, s), 7.68 (1H, s).

SYNTHESIS EXAMPLE 6:

Synthesis of 2-t-butyl-4-methyl-5-(p-trimethylsilyl benzyloxy)-3(2H)-pyridazinone (Compound No. 140)

To a solution of 0.9 g (0.005 mol) of 2-t-butyl-5-hydroxy-4-methyl-3(2H)-pyridazinone and 1.2 g (0.005 mol) of p-trimethylsilyl benzylbromide dissolved in 20 ml of N,N-dimethylformamide was added 1.0 g (0.007 mol) of potassium carbonate at room temperature under stirring. After addition, the resulting mixture was stirred at 120° C. for three hours. After allowed to cool, the reaction mixture was poured into 200 ml of water and extracted with 100 ml of benzene. The resulting benzene layer was washed with 100 ml of water, dried over anhydrous sodium sulfate, and freed of solvent by distillation to give 1.8 g of crude product. The crude product was recrystallized from 20 ml of hexane to obtain 1.2 g of 2-t-butyl-4-methyl-5-(p-trimethylsilyl benzyloxy)-3(2H)-pyridazinone.

M.P.: 93.5°~95.5° C.

NMR (CDCl₃, δ, TMS): 0.27 (9H, s), 1.62 (9H, s), 2.07 (3H, s), 5.16 (2H, s), 7.33 (2H, d, J=8 Hz), 7.58 (2H, d, J=8 Hz), 7.60 (1H, s).

SYNTHESIS EXAMPLE 7:

Synthesis of 2-t-butyl-5-(p-cyclohexyl-α-methyl-benzyloxy)-4-methyl-3(2H)-pyridasinone (Compound No. 143)

To 3 ml of dry N,N-dimethylformamide was added 0.24 g of 55% sodium hydride. The resulting mixture was kept at 0° C. and added dropwise with a solution of 1 g of p-cyclohexyl-α-methyl-benzyl alcohol dissolved in 5 ml of N,N-dimethylformamide. After ten minutes passed, the resulting mixture was added dropwise with a solution of 1 g of 2-t-butyl-5-chloro-4-methyl-3(2H)-pyridazinone dissolved in 5 ml of N,N-dimethylformamide. After completion of dropwise addition, the resulting mixture was allowed to stand at room temperature overnight. The resulting solution was poured into 30 ml of water and extracted twice with 30 ml of diethyl ether. The resulting organic layer was dried over anhydrous sodium sulfate and freed of solvent by distillation under reduced pressure to give 1.43 g of crude product. The crude product was recrystallized from 3 ml of hexane to obtain 0.56 g of 2-t-butyl-5-(p-cyclohexyl-60 -methyl-benzyloxy)-4-methyl-3(2H)-pyridazinone.

M.P.: 73.0°~76.0° C.

NMR (CDCl₃, δ, TMS): 1.47 (3H, d, J=7 Hz), 1.55 (9H, s), 2.06 (3H, s), 1.20~2.10 (11H, m), 5.30 (1H, q, J=7 Hz), 7.18 (4H, s), 7.49 (1H, s).

SYNTHESIS EXAMPLE 8:

Synthesis of 2-t-butyl-5-[(3'-(p-t-butylphenyl)-2'-methyl-2'-prope-1'-yl]-4-methyl-3(2H)-pyridazinone (Compound No. 177)

To 10 ml of dry N,N-dimethylformamide was added 0.75 g of 55% sodium hydride. The resulting mixture was kept at 0° C. and was added dropwise with a solution of 2 g of 3-(p-t-butylphenyl)-2-methyl-2-propenol dissolved in 15 ml of N,N-dimethylformamide. After ten minutes passed, the resulting solution was added dropwise with a solution of 2 g of 2-t-butyl-5-chloro-4-methyl-3(2H)-pyridazinone dissolved in 15 ml of N,N-dimethylformamide. After completion of dropwise addition, the resulting mixture was reacted at 80° C. for one hour. The resulting solution was poured into 50 ml of water and extracted twice with 50 ml of diethyl ether. The resulting organic layer was dried over anhydrous sodium sulfate and freed of solvent under reduced pressure to give crude product. The crude product was added with hexane and the crystals thus precipitated were purified and separated by means of thin layer chromatography (benzene/ethyl acetate=9) to obtain 2.5 g of 2-t-butyl-5-[3'-(p-t-butylphenyl)-2'-methyl-2'-prope-1'-yl]-4-methyl-3(2H)-pyridazinone.

M.P.: 89.0°~91.0° C.

NMR (CDCl₃, δ, TMS): 1.31 (9H, s), 1.62 (9H, s), 1.98 (3H, s), 2.07 (3H, s), 4.67 (2H, s), 6.53 (1H, bs), 7.28 (4H, m), 7.71 (1H, s).

SYNTHESIS EXAMPLE 9:

Synthesis of 2-t-butyl-5-(p-chlorobenzyloxy)-4-ethyl-3(2H)-pyridazinone (Compound No. 7)

To 10 ml of dry N,N-dimethylformamide was added 0.75 g of 55% sodium hydride. The resulting mixture was kept at 0° C. and was added dropwise with a solution of 2.2 g of 2-t-butyl-5-chloro-4-ethyl-3(2H)-pyridazinone dissolved in 15 ml of N,N-dimethylformamide. After ten minutes passed, the resulting mixture was added dropwise with a solution of 1.4 g of p-chlorobenzyl alcohol dissolved in 15 ml of N,N-dimethylformamide. After completion of dropwise addition, the resulting mixture was reacted at 80° C. for one hour. The resulting solution was poured into 50 ml of water and extracted twice with 50 ml of diethyl ether. The resulting organic layer was dried over anhydrous sulfate and freed of solvent by distillation under reduced pressure to give a crude product. The crude product was recrystallized from hexane to obtain 2.4 g of 2-t-butyl-5-(p-chlorobenzyloxy)-4-ethyl-3(2H)-pyridazinone.

M.P.: 86.0°~88.0° C.

NMR (CDCl₃, δ, TMS): 1.10 (3H, t, J=7 Hz), 1.61 (9H, s), 2.61 (2H, q, J=7 Hz), 5.13 (2H, s), 7.32 (4H, s), 7.67 (1H, s).

SYNTHESIS EXAMPLE 10:

Synthesis of 5-(p-t-butylbenzylthio)-2-ethyl-4-methyl-3(2H)-pyridazinone (Compound No. 164)

To 3 ml of dry N,N-dimethylformamide was added 0.024 g of 55% sodium hydride. The resulting mixture was kept at 0° C. and was added dropwise with a solution of 1 g of p-t-butylbenzyl mercaptan dissolved in 5 ml of N,N-dimethylformamide. After ten minutes passed, the resulting mixture was added dropwise with a solution of 0.67 g of 5-chloro-2-ethyl-4-methyl-3(2H)-pyridazinone dissolved in 5 ml of N,N-dimethylformamide. After completion of dropwise addition, the resulting mixture was allowed to stand over night. The resulting solution was poured into 30 ml of water and extracted twice with 30 ml of diethyl ether. The resulting organic layer was washed with water, dried over anhydrous sodium sulfate, and freed of solvent by distillation under reduced pressure to give 1.42 g of a crude product. The crude product was separated and purified by thin layer chromatography (silica gel, benzene) to obtain 0.69 g of 5-(p-t-butylbenzylthio)-2-ethyl-4-methyl-3(2H)-pyridazinone.

$N_D^{20} = 1.3823$.

NMR (CDCl₃, δ, TMS): 1.28 (9H, s), 1.30 (3H, t, J=8 Hz), 2.16 (3H, s), 4.10 (2H, q, J=8 Hz), 4.23 (2H, s), 7.27 (4H, s), 7.64 (1H, s).

SYNTHESIS EXAMPLE 11:

Synthesis of 2-t-butyl-4-butyl-5-(p-t-butylbenzylthio)-3(2H)-pyridazinone (Compound No. 162)

In 15 ml of N,N-dimethylformamide was dissolved 2.0 g (0.0092 mol) of 2-t-butyl-4-chloro-5-mercapto-3(2H)-pyridazinone. The resulting solution was added with 1.3 g (0.0123 mol) of anhydrous sodium carbonate and 1.6 g (0.0088 mol) of 4-t-butylbenzyl chloride, and then heated under stirring at 80°~110° C. for two hours. The resulting mixture was cooled to room temperature, and then added with 100 ml of water and stirred. The solid thus precipitated was filtered off, washed with water, dried, and recrystallized from ethanol to obtain 2.9 g of 2-t-butyl-5-(p-t-butylbenzylthio)-4-chloro-3(2H)-pyridazinone.

M.P.: 110.0°~112.0° C.

NMR (CDCl$_3$, δ, TMS): 1.29 (9H, s), 1.60 (9H, s), 4.21 (2H, s), 7.32 (4H, m), 7.61 (1H, s).

To a solution of 0.73 g (0.002 mol) of the 2-t-butyl-5-(p-t-butylbenzylthio)-4-chloro-3(2H)-pyridazinone thus obtained dissolved in 20 ml of tetrahydrofuran was added 3.0 ml of a solution of 10% butyl lithium dissolved in hexane at −70° C. under stirring. The reaction temperature was gradually raised from −70° C. to room temperature, and then the reaction mixture was stirred at room temperature for one hour. The reaction mixture was poured into 50 ml of ice water and extracted with 50 ml of chloroform. The resulting chloroform layer was washed with 100 ml of water, dried over anhydrous sodium sulfate and freed of solvent by distillation to give 0.65 g of a crude product. The crude product was purified by preparative thin layer chromatography on silica gel (developer:benzene) to obtain 0.38 g of 2-t-butyl-4-butyl-5-(p-t-butylbenzylthio)-3(2H)-pyridazinone.

$N_D^{20}$=1.5550.

NMR (CDCl$_3$, δ, TMS): 0.75~1.90 (7H, m), 1.29 (9H, s), 1.60 (9H, s), 2.45~2.85 (2H, m), 4.11 (2H, s), 7.26 (4H, s), 7.59 (1H, s).

M/Z: 386 (p+), 345, 331, 288, 239, 183, 161, 147 (BP).

SYNTHESIS EXAMPLE 12:

Synthesis of
2-tert.-butyl-5-(2'-butenylthio)-4-chloro-3(2H)-pyridazinone (Compound No. 201)

In 30 ml of N,N-dimethylformamide were dissolved 2.2 g (0.01 mol) of 2-tert.-butyl-4-chloro-5-mercapto-3(2H)-pyridazinone and 1.0 g (0.011 mol) of crotyl chloride, and 1.3 g of anhydrous sodium carbonate was added thereto. The resulting solution was stirred at 60° to 70° C. for 4 hours, poured into water and then extracted with benzene. The benzene layer was dried over anhydrous sodium sulfate and freed of solvent by distillation under reduced pressure. The resulting crystals were recrystallized from a mixed solvent of benzene and n-hexane to give 2.1 g of the captioned product.

M.P.: 72.0°~75.0° C.

NMR (CDCl$_3$, δ, TMS): 1.63 (9H, s), 1.70 (3H, d, J=7 Hz), 3.63 (2H, d, J=7 Hz), 5.65 (2H, m), 7.57 (1H, s).

SYNTHESIS EXAMPLE 13:

Synthesis of
4-chloro-2-ethyl-5-(3'-methyl-2'-butenyloxy)-3(2H)-pyridazinone (Compound No. 205)

In 30 ml of N,N-dimethylformamide were dissolved 1.7 g (0.01 mol) of 4-chloro-2-ethyl-5-hydroxy-3(2H)-pyridazinone and 1.5 g (0.01 mol) of 1-bromo-3-methyl-2-butene, and 1.8 g of anhydrous potassium carbonate was added thereto. The reaction mixture was stirred at 100° to 120° C. for 3 hours, and the resulting solution was poured into water and then extracted with benzene. The benzene layer was dried over anhydrous sodium sulfate and freed of solvent by distillation under reduced pressure. The resulting crystals were recrystallized from a mixed solvent of benzene and n-hexane to give 1.5 g of the captioned product.

M.P.: 72.0°~73.0° C.

NMR (CDCl$_3$, δ, TMS): 1.35 (3H, t, J=7 Hz), 1.77 (6H, s), 4.20 (2H, q, J=7 Hz), 4.74 (2H, d, J=7 Hz), 5.43 (1H, t, J=7 Hz), 7.72 (1H, s).

SYNTHESIS EXAMPLE 14:

Synthesis of
4-bromo-2-ethyl-5-(3'-phenyl-2'-propenyloxy)-3(2H)-pyridazinone (Compound No. 224)

In 50 ml of N,N-dimethylformamide were dissolved 2.8 g (0.01 mol) of 4,5-dibromo-2-ethyl-3(2H)-pyridazinone and 1.4 g (0.01 mol) of cinnamyl alcohol, and 0.7 g of powdery potassium hydroxide was added thereto. The resulting solution was stirred overnight at room temperature, and then poured into water and extracted with benzene. The benzene layer was dried over anhydrous sodium sulfate and freed of solvent by distillation under reduced pressure. The resulting crystals were recrystallized from a mixed solvent of ethyl alcohol and water to give 2.7 g of the captioned product.

M.P.: 117.0°~118.5° C.

NMR (CDCl$_3$, δ, TMS): 1.34 (3H, t, J=7 Hz), 4.21 (2H, q, J=7 Hz), 4.93 (2H, d, J=7 Hz), 6.30 (1H, t-d, J=7 Hz, 16 Hz), 6.79 (1H, d, J=16 Hz), 7.35 (5H, s), 7.75 (1H, s).

SYNTHESIS EXAMPLE 15

Synthesis of
2-tert.-butyl-4-chloro-5-(1'-methyl-3'-phenyl-2'-propenylthio-3(2H)-pyridazinone (Compound No. 229)

In 30 ml of N,N-dimethylformamide were dissolved 2.2 g (0.01 mol) of 2-tert.-butyl-4-chloro-5-mercapto-3(2H)-pyridazinone and 1.8 g (0.011 mol) of 3-chloro-3-methyl-1-phenyl-1-propene, and then 1.4 g of anhydrous sodium carbonate was added thereto. The mixture was stirred at 70° to 90° C. for 3 hours. The resulting solution was poured into water and then extracted with benzene. The benzene layer was dried over anhydrous sodium sulfate and freed of solvent by distillation under reduced pressure. The resulting crystals were recrystallized from a mixed solvent of benzene and n-hexane to give 2.2 g of the captioned product.

M.P.: 126.0°~128.0° C.

NMR (CDCl$_3$, δ, TMS): 1.60 (3H, d, J=7 Hz), 1.62 (9H, s), 4.30 (1H, q-d, J=7 Hz, 7 Hz), 6.13 (1H, d-d, J=16 Hz, 7 Hz), 6.68 (1H, d, J=16 Hz), 7.37 (5H, s), 7.77 (1H, s).

SYNTHESIS EXAMPLE 16:

Synthesis of
2-tert.-butyl-4-chloro-5-[3'-(4''-chlorophenyl)-2'-propenylthio]-3(2H)-pyridazinone (Compound No. 248)

In 30 ml of N,N-dimethylformamide were dissolved 2.2 g (0.01 mol) of 2-tert.-butyl-4-chloro-5-mercapto-3(2H)-pyridazinone and 1.9 g (0.01 mol) of p-chlorocinnamyl chloride, and then 1.8 g of anhydrous potassium carbonate was added thereto. The mixture was stirred at 70° to 90° C. for 3 hours. The resulting solution was poured into water and then extracted with benzene. The benzene layer was dried over anhydrous sodium sulfate and freed of solvent by distillation under reduced pressure. The resulting crystals were recrystallized from a mixed solvent of benzene and n-hexane to give 2.4 g of the captioned product.

M.P.: 111.0°~112.0° C.

NMR (CDCl$_3$, δ, TMS): 1.63 (9H, s), 3.85 (2H, d, J=7 Hz), 6.18 (1H, t-d, J=7 Hz, 16 Hz), 6.67 (1H, d, J=16 Hz), 7.27 (4H, s), 7.65 (1H, s).

SYNTHESIS EXAMPLE 17:

Synthesis of 2-tert.-butyl-4-chloro-5-[3'-(3", 4"-dichlorophenyl)-2'-propenylthio]-3(2H)-pyridazinone (Compound No. 311)

In 50 ml of ethanol were dissolved 2.2 g (0.01 mol) of 2-tert.-butyl-4-chloro-5-mercapto-3(2H)-pyridazinone and 2.3 g (0.0105 mol) of 3,4-dichlorocinnamyl chloride, and then 0.7 g of powdery potassium hydroxide was added thereto. The mixture was stirred at room temperature for 5 hours. The resulting solution was poured into water and then extracted with benzene. The benzene layer was dried over anhydrous sodium sulfate and freed of solvent by distillation under reduced pressure. The resulting crystals were recrystallized from a mixed solvent of benzene and n-hexane to give 2.5 g of the captioned product.

M.P.: 128.0°~129.0° C.

NMR (CDCl$_3$, δ, TMS); 1.64 (9H, s), 3.89 (2H, d, J=7 Hz), 5.25 (1H, t-d, J=7 Hz, 16 Hz), 6.68 (1H, d, J=16 Hz), 7.10~7.60 (3H, m), 7.70 (1H, s).

SYNTHESIS EXAMPLE 18:

Synthesis of 2-tert.-butyl-4-chloro-5-[3'-(2"-methylphenyl)-2'-propenylthio]-3(2H)-pyridazinone (Compound No. 323)

In 50 ml of methanol were dissolved 2.2 g (0.01 mol) of 2-tert.-butyl-4,5-dichloro-3(2H)-pyridizone and 1.6 g (0.0105 mol) of o-methylcinnamyl mercaptane, and then 1.6 g of anhydrous sodium carbonate was added thereto. The mixture was stirred overnight. The resulting solution was poured into water and then extracted with benzene. The benzene layer was dried over anhydrous sodium sulfate and freed of solvent by distillation under reduced pressure. The resulting crystals were recrystallized from a mixed solvent of benzene and n-hexane to give 2.3 g of the captioned product.

M.P. : 82.0°~84.0° C.

NMR (CDCl$_3$, δ, TMS): 1.62 (9H, s), 2.29 (3H, s), 3.87 (2H, d, J=7 Hz), 6.10 (1H, t-d, J=7 Hz, 16 Hz), 6.89 (1H, d, J=16 Hz), 7.10~7.50 (4H, m), 7.70 (1H, s).

SYNTHESIS EXAMPLE 19:

Synthesis of 2-tert.-butyl-4-chloro-5-[3'-(4"-methylphenyl)-2'-propenyloxy]-3(2H)-pyridazinone (Compound No. 328)

In 50 ml of N,N-dimethylformamide were dissolved 2.0 g (0.01 mol) of 2-tert.-butyl-4-chloro-5-hydroxy-3(2H)-pyridazinone and 1.8 g (0.0108 mol) of p-methylcinnamyl chloride, and then 2.1 g of anhydrous potassium carbonate was added thereto. The mixture was stirred at 80° to 100° C. for 4 hours. The resulting solution was poured into water and then extracted with benzene. The benzene layer was washed with an aqueous solution of sodium hydroxide and then with water, dried over anhydrous sodium sulfate and freed of solvent by distillation under reduced pressure. The resulting crystals were recrystallized from a mixed solvent of benzenes and n-hexane to give 2.2 g of the captioned product.

M.P.: 137°~139.5° C.

NMR (CDCl$_3$, δ, TMS): 1.60 (9H, s), 2.32 (3H, s), 4.87 (2H, d, J=7 Hz), 6.18 (1H, t-d, J=7 Hz, 16 Hz), 6.68 (1H, d, J=16 Hz), 7.05 (2H, d, J=8 Hz), 7.25 (2H, d, J=8 Hz), 7.69 (1H, s).

SYNTHESIS EXAMPLE 20:

Synthesis of 2-tert.-butyl-5-[3'-(4"-tert.-butylphenyl)-2'-methyl-2'-propenyloxy]-4-chloro-3(2H)-pyridazinone (Compound No. 388)

In 50 ml of hexamethyl phosphoric triamide were dissolved 2.0 g (0.01 mol) of 2-tert.-butyl-4-chloro-5-hydroxy-3(2H)-pyridazinone and 2.3 g (0.01 mol) of 1-(p-tert.-butylphenyl)-3-chloro-2-methyl-1-propene, and then 1.6 g of anhydrous sodium carbonate was added thereto. The mixture was stirred at 70° to 100° C. for 5 hours. The resulting solution was poured into water and then extracted with benzene. The benzene layer was washed with an aqueous solution of sodium hydroxide and then with water, dried over anhydrous sodium sulfate and freed of solvent by distillation under reduced pressure. The resulting crystals were recrystallized from a mixed solvent of benzene and n-hexane to give 2.3 g of the captioned product.

M.P.: 141.7°~142.5° C.

NMR (CDCl$_3$, δ, TMS): 1.30 (9H, s), 1.63 (9H, s), 1.97 (3H, s), 4.75 (2H, s), 6.52 (1H, s), 7.23 (4H, m), 7.68 (1H, s).

SYNTHESIS EXAMPLE 21:

Synthesis of 2-tert.-butyl-5-[3'-(4"-tert.-butylphenyl)-3'-methyl-2'-propenylthiol]-4-chloro-3(2H)-pyridazinone (Compound No. 398)

In 50 ml of N,N-dimethylformamide were dissolved 2.2 g (0.01 mol) of 2-tert.-butyl-4-chloro-5-mercapto-3(2H)-pyridazinone and 2.3 g (0.01 mol) of 1-(p-tert.-butylphenyl)-3-chloro-1-methyl-1-propene, and then 1.7 g of anhydrous potassium carbonate was added thereto. The mixture was stirred at room temperature for 5 hours. The resulting solution was poured into water and then extracted with benzene. The benzene layer was dried over anhydrous sodium sulfate and freed of solvent by distillation under reduced pressure to give 2.8 g of the captioned product as a viscous liquid.

NMR (CDCl$_3$, δ, TMS): 1.29 (9H, s), 1.61 (9H, s), 2.12 (3H, s), 3.80 (2H, d, J=7 Hz), 5.81 (1H, t, J=7 Hz), 7.28 (4H, s), 7.62 (1H, s).

SYNTHESIS EXAMPLE 22:

Synthesis of 2-tert.-butyl-4-chloro-5-[3'-(4"-trifluoromethylphenyl)-2'-propenylthio]-3(2H)-pyridazinone (Compound No. 442)

In 50 ml of N,N-dimethylformamide were dissolved 2.2 g (0.01 mol) of 2-tert.-butyl-4-chloro-5-mercapto-3(2H)-pyridazinone and 2.3 g (0.0104 mol) of p-trifluoromethyl cinnamyl chloride, and then 1.6 g of anhydrous potassium carbonate was added thereto. The mixture was stirred at 80° to 100° C. for 4 hours. The resulting solution was poured into water and then extracted with benzene. The benzene layer was dried over anhydrous sodium sulfate and freed of solvent by distillation under reduced pressure. The resulting crystals were recrystallized from a mixed solvent of benzene and n-hexane to give 2.8 g of the captioned product.

M.P.: 75.0°~77.0° C.

NMR (CDCl$_3$, δ, TMS): 1.63 (9H, s), 3.65 (2H, d, J=7 Hz), 6.27 (1H, t-d, J=7 Hz, 16 Hz), 6.70 (1H, d, J=16 Hz), 7.47 (4H, m), 7.58 (1H, s).

SYNTHESIS EXAMPLE 23:

Synthesis of 2-tert.-butyl-4-chloro-5-[1′-methyl-3′-(4″-phenyl-phenyl)-2′-propenylthio]-3(2H)-pyridazinone (Compound No. 463)

In 50 ml of N,N-dimethylformamide were dissolved 2.2 g (0.01 mol) of 2-tert.-butyl-4-chloro-5-mercapto-3(2H)-pyridazinone and 2.5 g (0.0103 mol) of 3-chloro-3-methyl-1-(p-phenylphenyl)-1-propene, and then 1.6 g of anhydrous potassium carbonate was added thereto. The mixture was stirred at room temperature for 5 hours. The resulting solution was poured into water and then extracted with benzene. The benzene layer was dried over anhydrous sodium sulfate and freed of solvent by distillation under reduced pressure. The resulting crystals were recrystallized from a mixed solvent of benzene and n-hexane to give 2.7 g of the captioned product.

M.P.: 126.0°~129.5° C.

NMR (CDCl$_3$, δ, TMS): 1.55 (3H, d, J=7 Hz), 1.59 (9H, s), 4.24 (1H, q-d, J=7 Hz, 7 Hz), 6.14 (1H, d-d, J=16 Hz, 7 Hz), 6.62 (1H, d, J=16 Hz), 7.20~7.65 (9H, m), 7.69 (1H, s).

SYNTHESIS EXAMPLE 24:

Synthesis of 2-tert.-butyl-4-chloro-5-(3′-phenyl-2′-propynyloxy)-3(2H)-pyridazinone (Compound No. 494)

To 1.3 g (0.01 mol) of 3-hydroxy-1-phenyl-1-propyne was added 50 ml of N,N-dimethylformamide, and then 0.45 g of 55% sodium hydride was added thereto at 0° C. The resulting mixture was stirred for one hour. Thereafter, 2.2 g (0.01 mol) of 2-tert.-butyl-4,5-dichloro-3(2H)-pyridazinone was added thereto at room temperature and the mixture was stirred overnight at room temperature. The resulting solution was poured into water and then extracted with benzene. The benzene layer was dried over anhydrous sodium sulfate and freed of solvent by distillation under reduced pressure. The crystals thus obtained were recrystallized from benzene-n-hexane to give 2.0 g of the captioned product.

M.P.: 142.5°~146.5° C.

NMR (CDCl$_3$, δ, TMS): 1.62 (9H, s), 5.08 (2H, s), 7.33 (5H, bs,), 7.93 (1H, s).

When the compounds according to the present invention are used for insecticidal, acaricidal, nematicidal and/or fungicidal agents for agricultural and horticultural used or for expellents of ticks parasitic on animals, they are generally mixed with appropriate carriers, for instance, solid carriers such as clay, talc, bentonite or diatomaceous earth, or liquid carriers such as water, alcohols (e.g. methanol and ethanol), aromatic hydrocarbons (e.g. benzene, toluene and xylene), chlorinated hydrocarbons, ethers, ketones, acid amides (e.g. dimethylformamide) or esters (e.g. ethyl acetate). If desired, to these mixtures can be added a surfactant, emulsifier, dispersing agent, suspending agent, penetrating agent, spreader, stabilizer and the like to put them into practical uses in the form of liquid preparation, emulsifiable concentrate, wettable powder, dust, granule, flowable or the like. Moreover, the resulting mixtures may be incorporated with other herbicides, various insecticides, fungicides, plant-growth regulating agents and/or synergists during preparation of application thereof, as necessary.

The amount of the compounds of the invention to be used as an active ingredient is suitably in the range of 0.005 to 50 kg per hectare although it varies depending upon the place and the season where the compounds are applied, manner of application, diseases and insect pests to be applied, cultivated crops to be protected and the like.

In the following, there are shown component ratios of formulations and formulation examples of fungicidal, insecticidal, acaricidal and/or nematicidal compositions and expellent compositions for ticks parasitic on animals, said compositions containing the compounds of the present invention as an active ingredient. These examples are merely illustrative and not to restricts the invention. In the following examples, "part" means "part by weight".

1. COMPOSITION RATIO OF FORMURATION
(1) Emulsifiable concentrates
   active ingredients: 5–25 wt %
   liquid carrier: 52–90 wt % (Xylene, DMF, Methyl naphthalene, Cyclohexanone, Dichlorobenzene Isophorone)
   surface active agent: 5–20 wt % (Sorpol 2680, Sorpol 3005X, Sorpol 3346)
   others: 0–20 wt % (Piperonyl butoxide: 0–20 wt % Benzotriazole: 0–5 wt %)
(2) Oil solutions
   active ingredient: 5–30 wt %
   liquid carrier: 70–95 wt % (Xylene, Methyl cellosolve, Kerosene)
(3) Flowables
   active ingredient: 5–70 wt %
   liquid carrier: 12.4–78.4 wt % (water)
   surface active agent: 1–10.5 wt % (Lunox 1000C, Sorpol 3353, Soprophor FL, Nippol, Agrisol S-710, Lignin sulfonic acid soda)
   others: 0–10 wt % (Formalin 0–0.3 wt %, Ethylene glycol 0–10 wt %, Propylene glycol 0–10 wt %)
(4) Wettable powders (W.P.)
   active ingredient: 5–70 wt %
   solid carrier: 15–89 Wt % (Calcium carbonate Kaolinite, Zeeklite D, Zeeklite PFP, Diatomaceous earth, Talc)
   surface active agent: (Sorpol 5039, Lunox 1000C, Lignin Sulfonic acid calcium, Sodium dodecyl-sulfonate, Sorpol 5050, Sorpol 005D, Sorpol 5029-0)
   others: 0–5 wt % (Carplex #80)
(5) Dusts
   active ingredient: 0.1–30 wt %
   solid carrier: 67–98 wt % (Calcium carbonate, Kaolinite, Zeeklite, Talc)
   others: 0–3 wt % (Diisopropylphosphate: 0–1.5 wt %, Carplex #80: 0–3 wt %)
(6) Granules
   active ingredient: 0.5–30 wt %
   solid carrier: 67–99 wt % (Calcium carbonate, Kaolinite, Talc, Bentonite)
   others: 0–8 wt % (Lignin sulfonic acid calcium: 0–3 wt %, polyvinylalcohol 0–5 wt %)
2. FORMULATION EXAMPLES
Formulation Example 1: Emulsifiable concentrates

| | |
|---|---|
| Active ingredient | 20 parts |
| Xylene | 55 parts |
| N,N—dimethylformamide | 20 parts |
| Solpol 2680 (trade name, a mixture of a non-ionic surface-active agent and an anionic surface-active agent manufactured by Toho Chemicals, Co., | |

-continued

| | |
|---|---|
| Ltd., Japan) | 5 parts |

The above components are mixed intimately together to form an emulsifiable concentrate. Upon use, the emulsifiable concentrate is diluted with water up to one fifteenth to one twenty thousandth in concentration and applied at a rate of 0.005 to 50 kg of the active ingredient per hectare.

| Formulation Example 2: Wettable powders | A | B |
|---|---|---|
| Active ingredient | 25 parts | 25 parts |
| Siegreit PFP (trade name, a mixture of caolinite and sericite manufactured by Siegreit Mining Industries Co., Ltd.) | 66 parts | 69 parts |
| Solpol 5039 (trade name, and anionic surface-active agent manufactured by Toho Chemical Co., Ltd., Japan) | 4 parts | 3 parts |
| Carplex #80 (trade name, white carbon manufactured by Shionogi Seiyaku K. K., Japan) | 3 parts | 3 parts |
| Calcium lignin sulfonate | 2 parts | — |

The above components are homogeneously mixed together and ground to form a wettable powder. Upon use, the wettable powder is diluted with water up to one fifteenth to one twenty thousandth and applied at a rate of 0.005 to 50 kg of the active ingredient per hectare.

| Formulation Example 3: Oil solutions | A | B |
|---|---|---|
| Active ingredient | 10 parts | 30 parts |
| methylcellosolve | 90 parts | 70 parts |

The above components are homogeneously mixed together to form an oil solution. Upon use, the oil solution is applied at a rate of 0.005 to 50 kg of the active ingredient per hectare.

| Formulation Example 4: Dusts | |
|---|---|
| Active ingredient | 3.0 parts |
| Carplex #80 (trade name, white carbon as mentioned in the above) | 0.5 part |
| Clay | 95 parts |
| di-isopropyl phosphate | 1.5 parts |

The above components are homogeneously mixed together and ground to form dust. Upon use, the dust is applied at a rate of 0.005 to 50 kg of the active ingredient per hectare.

| Formulation Example 5: Granules | |
|---|---|
| Active ingredient | 5 parts |
| Bentonite | 54 parts |
| Talc | 40 parts |
| Calcium lignin sulfonate | 1 part |

The above components are mixed intimately together and ground, incorporated with a small amount of water and mixed together with stirring. The resulting mixture is granulated by means of extrusion-granulator and dried to form granules. Upon use, the granule is applied at a rate of 0.005 to 50 kg of the active ingredient per hectare.

| Formulation Example 6: Flowables | |
|---|---|
| Active ingredient | 25 parts |
| Solpol 3353 (trade name, a non ionic surface-active agent manufactured by Toho Chemicals, Co., Ltd., Japan) | 10 parts |
| Runox 1000C (trade name, an anionic surface-active agent manufactured by Toho Chemicals, Co., Ltd., Japan) | 0.5 part |
| 1% aqueous solution of Xanthan gum (natural high-molecular compound) | 20 parts |
| Water | 44.5 parts |

The above components except the active ingredient are uniformly mixed together to form a solution, and thereto is added the active ingredient. The resulting mixture is thoroughly stirred, wet-ground by means of sand mill to form a flowable. Upon use, the flowable is diluted up to one fiftieth to one twenty thousandth with water and applied at a rate of 0.005 to 50 kg of the active ingredient per hectare.

The compounds according to the present invention not only exhibit superior insecticidal action on hemiptera insect pests such as green rice leafhopper (*Nephotettix cincticeps*), lepidoptera insect pests such as diamondback moth (*Plutella xylostella*), coleoptera insect pests and sanitary insect pests such as pale house mosquito (*Culex pipiens*), but are also useful for expelling mites parasitic on fruits and vegetables such as two-spotted spider mites (*Tetranychus urticae*), Kanzawa spider mite (*Tetranychus kanzawai*), Carmine spider mite (*Tetranychus cinnabarinus*), citrus red mite (*Panonychus citri*) and European red mite (*Panonychus ulmi*), as well as ticks parasitic on animals such as southern cattle tick (*Boophilus microplus*), cattle tick (*Boophilus annulatus*), galf coast tick (*Amblyomma maculatum*), brown-ear tick (*Rhipicephalus appendiculatus*) and (*Haemaphysalis longicornis*). The compounds of the invention are also useful for controlling nematoda such as root-knot nematode (*Meloidogyne spp.*). The main features of the compounds of the present invention resides in that the compounds are useful for the prevention or control of diseases of fruits and vegetables such as powdery mildew, downy mildew, etc. in addition to having the above mentioned insecticidal, acaricidal and nematicidal actions. Accordingly, the compounds of the present invention are an excellent agricultural drug which enables control of pests and diseases simultaneously. Moreover, they are excellent as an expellent for ticks parasitic on animals such as domestic animals (e.g. cattle, horse, sheep and pig), domestic fowls, and other animals such as dog, cat, rabbit and the like.

The invention is further explained in detail by way of the following test examples.

TEST EXAMPLE 1

Insecticidal test on Green rice leafhopper (*Nephotettix cincticeps*)

Stems and leaves of paddy were immersed into 500 ppm or 1000 ppm emulsion of each compound of the invention for about 10 seconds, and then the stems and leaves were placed into a glass cylinder. After 10 adults of green rice leafhopper which would show resistance to organic phosphorus type insecticides were released, the glass cylinder was covered with a plastic cap having some pores and placed in a thermostatic chamber kept at 25° C. After 96 hours later, the mortality was determined according to the following equation:

$$\text{Mortality (\%)} = \frac{\text{number of the insect killed}}{\text{number of the insect placed}} \times 100$$

Incidentally, the test was repeated twice for each compound.

The results thereof are listed in Tables 5 and 6.

TEST EXAMPLE 2

Contact insecticidal test on 28-spotted Lady Beetle (*Henosepilachna vigintioctopunctata*)

A leaf tomato was immersed in an aqueous emulsion containing 500 ppm or 1000 ppm of each compound of the invention and then air-dried. The leaf thus treated was placed in a laboratory dish, into which 10 second inster 28-spotted lady beetle larvae were released. The dish was then fitted with a cap provided with pores and then placed in a thermostatic chamber kept at 25° C. The number of the larvae killed was checked after 96 hours and the mortality thereof was determined in the same manner as in Test Example 1. Incidentally, the test was repeated twice for each compound.

The test results are shown in Tables 5 and 6.

TEST EXAMPLE 3

Acaricidal test on Kanzawa Spider Mite (*T. Kanzawa*)

A leaf of kidney bean was cut into a round piece of 1.5 cm in diameter by a leaf punch, and then placed on the moistened filter paper put on a styrol cup of 7 cm in diameter. Each piece of the leaf was inoculated with 10 Kanzawa Spider Mite nymphs. Half a day after the inoculation, each 2 ml of an aqueous emulsion containing 500 ppm or 1000 ppm of a compound of the present invention diluted with a spreader was applied to each styrol cup by means of a rotary spray tower. The number of the nymph killed was checked after 96 hours and the mortality of the nymph was determined as in Test Example 1. Incidentally, the test was repeated twice for each compound.

The results are shown in Tables 5 and 6.

TABLE 5

| Compound No. | Green rice leafhopper (*Nephotettix cincticeps*) (500 ppm) | 28-spotted lady beetle (*Henosepilachna vigintioctopunctata*) (500 ppm) | Kanzawa spider mite (*T. Kanzawa*) (500 ppm) |
|---|---|---|---|
| 3 | 100 | 100 | 100 |
| 5 | 100 | 100 | 100 |
| 7 | — | 100 | — |
| 11 | 100 | 70 | 100 |
| 17 | 100 | 100 | 100 |
| 24 | 100 | 100 | — |
| 30 | 100 | 100 | 100 |
| 31 | — | — | 100 |
| 33 | 90 | 90 | 100 |
| 34 | 100 | 100 | 100 |
| 36 | 100 | 100 | 100 |
| 38 | 100 | 100 | 100 |
| 43 | 100 | 100 | 100 |
| 45 | — | — | 100 |
| 47 | 75 | 100 | 100 |
| 49 | 100 | 100 | 100 |
| 53 | 100 | 100 | 100 |
| 55 | 100 | 100 | 100 |
| 59 | 60 | 100 | 100 |
| 60 | — | — | 100 |
| 61 | 80 | 100 | 100 |
| 68 | 100 | 100 | 100 |
| 82 | 100 | 100 | 100 |
| 87 | 100 | 100 | 100 |
| 89 | 100 | 100 | 100 |
| 91 | 100 | 100 | 100 |
| 95 | 100 | 100 | 100 |
| 98 | 100 | 100 | 100 |
| 100 | 100 | 100 | 100 |
| 107 | 100 | 100 | 100 |
| 108 | — | 100 | — |
| 140 | 100 | — | 100 |
| 141 | 100 | 100 | 100 |
| 143 | 100 | 100 | 100 |
| 145 | 100 | 100 | 100 |
| 147 | 100 | 100 | 100 |
| 150 | 100 | 100 | 100 |
| 155 | 100 | — | 100 |
| 157 | 100 | 100 | 100 |
| 159 | 100 | 100 | 100 |
| 160 | — | — | 100 |
| 162 | — | — | 100 |
| 164 | 100 | 100 | 100 |
| 166 | 100 | — | 100 |
| 169 | 100 | — | 100 |
| 170 | 100 | 100 | 100 |
| 173 | 100 | 100 | 100 |
| 174 | 100 | — | 100 |
| 175 | — | — | 100 |
| 176 | 100 | 100 | 100 |
| 177 | 100 | 100 | 100 |
| 179 | — | — | 100 |
| 183 | 100 | 100 | 100 |
| 184 | 100 | — | 100 |
| 185 | 100 | 100 | 100 |
| 186 | 100 | 100 | 100 |
| 189 | 100 | 100 | 100 |
| 190 | 100 | 100 | 100 |
| 191 | 100 | 100 | 100 |
| 196 | 100 | 100 | 100 |
| 197 | 100 | 100 | 100 |

TABLE 6

| Compound No. | Green rice leafhopper (*Nephotettix cincticeps*) (1000 ppm) | 28-spotted lady beetle (*Henosepilachna vigintioctopunctata*) (1000 ppm) | Kanzawa spider mite (*T. Kanzawa*) (1000 ppm) |
|---|---|---|---|
| 201 | 100 | 100 | 100 |
| 202 | 100 | 100 | 75 |
| 215 | 100 | — | 100 |
| 216 | — | 100 | 100 |
| 227 | 100 | — | — |
| 228 | — | — | 100 |
| 229 | 100 | — | 100 |
| 240 | — | — | 100 |
| 241 | — | — | 100 |
| 248 | 100 | 100 | 100 |
| 255 | 100 | 100 | 100 |
| 268 | 100 | — | 100 |
| 269 | — | 100 | 100 |
| 301 | 100 | 100 | 100 |
| 311 | — | 100 | 100 |
| 312 | — | 100 | 100 |
| 322 | — | — | 100 |
| 323 | — | 100 | 100 |
| 328 | 100 | 100 | 100 |
| 335 | 100 | 100 | 100 |
| 336 | 100 | 100 | 100 |
| 362 | 100 | 100 | 100 |
| 363 | 100 | 100 | 100 |
| 373 | — | 100 | 100 |
| 374 | 100 | 100 | 100 |
| 375 | 100 | 100 | 100 |
| 382 | 100 | 100 | 100 |
| 383 | 100 | 100 | 100 |
| 384 | — | 100 | 100 |
| 388 | 100 | 100 | 100 |
| 394 | 100 | 100 | 100 |
| 395 | 100 | 100 | 100 |

TABLE 6-continued

| Compound No. | Green rice leafhopper (Nephotettix cincticeps) (1000 ppm) | 28-spotted lady beetle (Henosepilachna vigintioctopunctata) (1000 ppm) | Kanzawa spider mite (T. Kanzawa) (1000 ppm) |
|---|---|---|---|
| 398 | — | 100 | 100 |
| 399 | 100 | 100 | 100 |
| 442 | 100 | 100 | 100 |
| 463 | 100 | 100 | 100 |
| 464 | 100 | 100 | 100 |
| 494 | 100 | — | — |
| 515 | 100 | — | 100 |
| 516 | 100 | 100 | 100 |
| 521 | 100 | 100 | 100 |

TEST EXAMPLE 4

Insecticidal test on Common cutworm (*Spodoptera litura*)

A leaf of cabbage was immersed in an aqueous emulsion containing 500 ppm of each compound of the invention for about 10 seconds, and then air-dried. The leaf thus treated was placed in a dish, into which second instar common cutworm larvae were released. The dish was fitted with a cap provided with some pores and then placed in a thermostatic chamber kept at 25° C. The mortality of the common cutworm after 7 days was determined in the same manner as in Test Example 1. As the results, the following compounds showed a mortality of 100%:

Compound Nos. 36, 38, 43, 47, 49, 91, 98, 145, 147, 150, 177 and 183.

TEST EXAMPLE 5

Insecticidal test on Diamondback Moth (*Plutella xylostella*)

A leaf of cabbage was immersed in an aqueous emulsion containing 500 ppm of each compound of the invention for about 10 seconds, and then air-dried. The leaf thus treated was placed in a dish, into which second instar diamondback moth larvae were released. The dish was fitted with a cap provided with some pores and then placed in a thermostatic chamber kept at 25° C. The mortality of the diamondback moth after 7 days was determined in the same manner as in Test Example 1. As the results, the following compounds showed a mortality of 100%:

Compound Nos. 248, 255, 301, 322, 323, 328, 335, 336, 363, 382, 383, 384, 442 and 463.

TEST EXAMPLE 6

Insecticidal test of Green rice leafhopper (*Nephotettix cincticeps*) (low concentration test)

In accordance with Test Example 1, all the compounds tested showed high efficacy against Green rice leafhopper. Incidentally, the test carried out by using four kinds of emulsions containing a compound of the invention or a reference compound in a concentration of 1000, 500, 100 and 10 ppm, respectively. The results are shown in Tables 7 and 8.

It is shown from the results thereof that the compounds of the invention exhibit much higher insecticidal activity than known reference compounds.

TABLE 7

The compound of the formula:

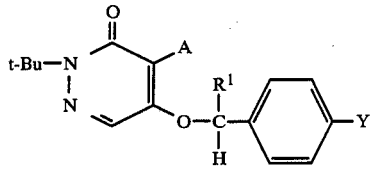

| | Present Compound | | Reference Compound[a] | |
|---|---|---|---|---|
| | A | | Cl | |
| | CH₃ | | | |
| | R¹ | | | |
| Y | H | CH₃ | H | CH₃ |
| F | 100[b] | 100 | 90 | 100 |
| | 100 | 100 | 0 | 100 |
| | 100 | 100 | — | 0 |
| | (No. 3)[c] 60 | (No. 4) 90 | — | — |
| Cl | 100 | | 80 | |
| | 100 | | 0 | |
| | 100 | | — | |
| | (No. 11) 80 | | — | |
| ⌬-H | | | 100 | 95 |
| | | | 100 | 0 |
| | | | 100 | — |
| | | (No. 143) 55 | | — |
| OC₅H₁₁ | 100 | | 100 | |
| | 100 | | 100 | |
| | 100 | | 70 | |
| | (No. 95) 95 | | 0 | |
| CH₃-⌬-OCH₂- | 100 | | 100 | |
| | 100 | | 50 | |
| | 100 | | — | |
| | (No. 107) 60 | | — | |

[a] The compound described and claimed in European laid-open Patent Specification No. 0088384.
[b] Mortalities (%) at the concentrations of 1000, 500, 100 and 10 ppm (from the top line to the bottom), respectively.
[c] Compound No. of the invention.

TABLE 8

The compound of the formula:

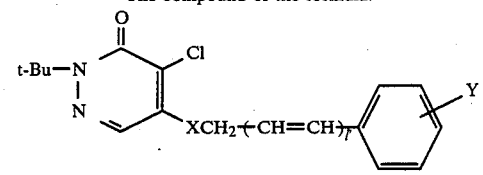

| X, Y | Present Compound (l' = 1) | | Reference Compound (l' = 0) |
|---|---|---|---|
| | 100[c] | | 100[a] |
| X = S | 100 | | 90 |
| Y = 4-Cl | 100 | (Compound No. 248) | 80 |
| | 95 | | 40 |
| | 100 | | 80[b] |
| X = O | 100 | | 0 |
| Y = 4-CH₃ | 100 | (Compound No. 328) | — |
| | 40 | | — |
| | 100 | | 75[b] |
| X = O | 100 | | 0 |
| Y = 2, 4-Cl₂ | 100 | (Compound | — |

TABLE 8-continued

The compound of the formula:

t-Bu—N(—N=)—C(=O)—C(Cl)=C(XCH$_2$(CH=CH)$_{l'}$—C$_6$H$_4$—Y)—CH=

| X, Y | Comp. Present Compound ($l' = 1$) | Reference Compound ($l' = 0$) |
|---|---|---|
| | 60 (No. 301) | — |

[a] The compound described and claimed in Japanese laid-open Patent Specification Sho 60-4173.
[b] The compound described and claimed in European laid-open Patent Specification No. 0088384.
[c] Mortalities (%) at the concentrations of 1000, 500, 100 and 10 ppm (from the top line to the bottom), respectively.

TEST EXAMPLE 7

Contact insecticidal test on 28-spotted Lady Beetle (*Henosephilachna vigintioctopunctata*) (low concentration test)

In accordance with Test Example 2, all the compounds tested showed high efficacy against 28-spotted Lady Beetle. Incidentally, the test was carried out by using four kinds of emulsions containing a compound of the invention or a reference compound in a concentration of 1000, 500, 100 and 10 ppm, respectively. The results are shown in Tables 9 and 10.

It is shown from the results thereof that the compounds of the invention exhibit much higher insecticidal activity than known reference compounds.

TABLE 9

The compound of the formula:

t-Bu—N(—N=)—C(=O)—C(A)=C(O—C(R$^1$)(H)—C$_6$H$_4$—Y)—CH=

| Y | Comp. Present Compound | | Reference Compound[a] | |
|---|---|---|---|---|
| | A | | | |
| | CH$_3$ | | Cl | |
| | R$^1$ | | | |
| | H | CH$_3$ | H | CH$_3$ |
| 4-C$_6$H$_5$— | 100[b] | 100 | | |
| | 100 | 100 | | |
| | 100 | 40 | | |
| | (No. 47)[c] 55 | 0 | | |
| 4-Cl-C$_6$H$_4$— | 100 | 100 | | |
| | 100 | 100 | | |
| | 100 | 40 | | |
| | (No. 36) 50 | 30 | | |

[a] The compound described and claimed in European laid-open Patent Specification No. 0088384.
[b] Mortalities (%) at the concentrations of 1000, 500, 100 and 10 ppm (from the top line to the bottom), respectively.
[c] Compound No. of the invention.

TABLE 10

The compound of the formula:

t-Bu—N(—N=)—C(=O)—C(Cl)=C(XCH$_2$(CH=CH)$_{l'}$—C$_6$H$_4$—Y)—CH=

| X, Y | Comp. Present Compound ($l' = 1$) | Reference Compound ($l' = 0$) |
|---|---|---|
| | 100[c] | 100[a] |
| X = S | 100 | 50 |
| Y = 2-CH$_3$ | 85 (Compound No. 323) | 0 |
| | 20 | — |
| | 100 | 80[b] |
| X = 0 | 100 | 0 |
| Y = 4-CH$_3$ | 80 (Compound No. 328) | — |
| | 55 | — |
| | 100 | 75[b] |
| X = 0 | 100 | 0 |
| Y = 3,4-Cl$_2$ | 85 (Compound No. 312) | — |
| | 50 | — |
| | 100 | 100[a] |
| X = S | 100 | 100 |
| Y = 4-Cl | 100 (Compound No. 248) | 20 |
| | 75 | 0 |

[a] The compound described and claimed in Japanese laid-open Patent Specification Sho 60-4173.
[b] The compound described and claimed in European laid-open Patent Specification No. 0088384.
[c] Mortalities (%) at the concentrations of 1000, 500, 100 and 10 ppm (from the top line to the bottom), respectively.

TEST EXAMPLE 8

Test for controlling Downy mildew of cucumber

Employing cucumbers (*Cucumis sativus L.*: variety Sagamihanjiro) which had been grown for 2 weeks, thereto was sprayed a solution of an emulsified concentrate according to the invention which had been adjusted to a predetermined concentration (1000 ppm) at the rate of 20 ml per pot. After each pot was placed overnight in a greenhouse, a suspension of spores of *Pseudoperonospora cubensis* (the concentration of the spores being such that when observed by a 150 magnification microscope, 15 pieces of the spore may be present) was sprayed to the cucumbers for inoculation. The cucumbers to which the spores of *Pseudoperonospora cubensis* had been inoculated were left for 24 hours in a room kept at 25° C. with a relative humidity of 100% and then transported to a greenhouse for observation of disease appearance. Seven days after the inoculation, the percentages of the disease appearance were measured.

As the results, no disease was observed at all with respect to the following compounds.

Compound Nos. 3, 11, 17, 24, 36, 38, 43, 45, 49, 55, 91, 140, 143, 157, 166, 169, 186, 196, 255, 322, 323, 384, 442 and 494.

TEST EXAMPLE 9

Test for controlling Powdery mildew of cucumber

Employing cucumbers (*Cucumis sativus L.*: variety Sagamihanjiro) which had been grown in pots for 2 weeks, thereto was sprayed a solution of an emulsifiable concentrate according to the present invention which had been adjusted to a predetermined concentration (1000 ppm) at the rate of 20 ml per pot. After each pot was placed overnight in a greenhouse, a suspension of spores of *Sphaerotheca fuliginea* (the concentration of the spores being such that when observed by a 150 magnification microscope, 25 pieces of the spores may be present) was sprayed to the cucumbers for inoculation. The cucumbers were placed in a greenhouse at 25°~30° C. for observation of disease appearance. Ten days after the inoculation, the percentages of the disease appearance were measured.

As the results, no diseases was observed at all with respect to the following compounds.

Compound Nos. 3, 11, 24, 30, 34, 36, 38, 43, 45, 47, 49, 55, 59, 87, 91, 100, 140, 141, 143, 145, 147, 155, 157, 159, 166, 169, 170, 179, 186, 322, 323, 363, 388, 399, 442 and 516.

TEST EXAMPLE 10

Test for controlling leaf rust (*Puccinia recondita*) of wheat

Employing wheats (Norin 61, 3 to 4 leaf-stage) which had been grown in a pot of 9 cm in diameter, thereto was sprayed a solution of an emulsifiable concentrate according to the invention which had been adjusted to a concentration of 1000 ppm at the rate of 20 ml per pot. Next day after application, a suspension of spores of *Pussinia recondita* (the concentration of the spores being such that when observed by a 150 magnification microscope, 30 pieces of the spore may be present) was sprayed to the wheats for inoculation. The wheats to which the spores of *Puccinia recondita* had been inoculated were left for 24 hours in a box kept at 25° C. with a relative humidity of 95%. Thereafter, the wheats were kept at room temperature. Ten days after the inoculation, the area of the wheat having disease appearance was measured and protective value was calculated according to the following equation:

$$\text{Protective value (\%)} = \left(1 - \frac{\text{area having disease appearance in treated plot}}{\text{area having disease appearance in untreated plot}}\right) \times 100$$

As the results, the following compounds showed a protective value of 100%.

Compounds Nos. 3, 5, 17, 24, 30, 36, 38, 43, 45, 55, 91, 140, 141, 145, 147, 155, 157, 159, 166, 169 and 170.

TEST EXAMPLE 11

Test for controlling Rice Blast (*Pyricularia oryzae*) of rice plant

Employing rice-plants (Nihonbare, 3 to 4 leaf-stage) which had been grown in a pot of 9 cm in diameter, thereto was sprayed a solution of an emulsifiable concentrate according to the invention which had been adjusted to a concentration of 1000 ppm at the rate of 20 ml per pot. Next day after application, a suspension of spores of *Pyricularia oryzae* (the concentration of the spores being such that when observed by a 150 magnification microscope, 40 pieces of the spore may be present) was sprayed to the rice plant for inoculation. The rice plants to which the spores of *Pyricularia oryzae* had been inoculated were left for 24 hours in a box kept at 25° C. with a relative humidity of 95%. Thereafter, the rice plants were kept at room temperature. Ten days after inoculation, the area of the rice plant having disease appearance was measured and protective value was calculated as in Test Example 10.

As the results, the following compounds showed a protective value of 100%.

Compound Nos. 3, 17, 24, 29, 30, 34, 36, 43, 45, 47, 49, 55, 87, 91, 140, 141, 147, 150, 164, 169, 240, 248, 322, 323, 335 and 516.

TEST EXAMPLE 12

Test for controlling Downy mildew of cucumber (low concentration test)

In accordance with Test Example 8, all the compounds tested showed high efficacy against downy-mildew of cucumber. Incidentally, the test was carried out by using an emulsion containing 500, 100 and 50 ppm of a compound of the invention or a reference compound. And protective value was determined as in Test Example 10. The results thereof are shown in Tables 11 and 12.

It is shown from the results in the tables that the compounds of the invention exhibit much higher fungicidal activity than the known reference compounds.

TABLE 11

The compound of the formula:

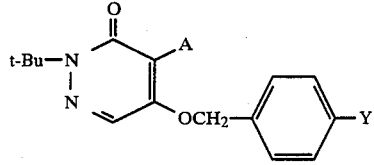

| Y | Comp. A | Present Compound CH₃ | Reference Compound[a] Cl |
|---|---|---|---|
| F | | 100 | 0 |
| | (No. 3)[c] | 90[b] | 0 |
| | (No. 47) | 100 | 0 |
| ⟨phenyl⟩ | | 100 | 0 |
| | (No. 108) | 100 | |
| | | 80 | 0 |
| —OCH₂—⟨C₆H₄⟩—F | | | |

[a]The compound described and claimed in European laid-open Patent Specification No. 0088384.
[b]Protective values (%) at the concentrations of 500 ppm (upper) and 100 ppm (lower), respectively.
[c]Compound No. of the invention.

TABLE 12

The compound of the formula:

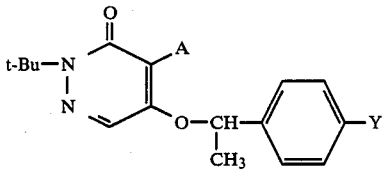

| Y | Comp. A | Present Compound CH₃ | Reference Compound[a] Cl |
|---|---|---|---|
| H | (No.143)[c] | 100[b] | 70 |
| | | 100 | 0 |
| | | 60 | — |

TABLE 12-continued

The compound of the formula:

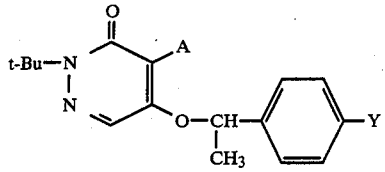

| Y | Comp. A | Present Compound CH₃ | Reference Compound[a] Cl |
|---|---|---|---|
| 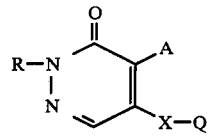 | (No. 37) | 100<br>100<br>50 | 40<br>0<br>— |

[a] The compound described and claimed in European laid-open Patent Specification No. 0088384.
[b] Protective values (%) at the concentrations of 500, 100 and 50 ppm (from the top line to the bottom), respectively.
[c] Compound No. of the invention.

TEST EXAMPLE 13

Nematicidal test on Root-knot Nematode (*Meloidogyne spp.*)

Soil contamination with root-knot nematode was placed in a styrol cup of 8 cm in diameter. A liquid containing 1000 ppm of an active ingredient was prepared by diluting an emulsifiable concentration according to the present invention with water and then a spreader was added thereto. The soil contaminated with namatode and placed int he stryol cup was drenched with each 50 ml of the resulting liquid. After 48 hours, a tomato seedling as an indicator was transplanted into the soil thus treated. 30 days after the transplantation, the roots of the tomato were washed with water and the root-knot parasitism was checked by observation and evaluation according to the following rating:

Rating of root-knot parasitism
0: no root-knot observed at all
1: a few root-knots observed
2: a medium number of root-knot observed
3: many root-knots observed
4: considerably many root-knots observed Incidentally, the test was repeated twice for each compound. The results are shown in Table 13.

TABLE 13

| Compound No. | Root-knot parasitism | Compound No. | Root-knot parasitism |
|---|---|---|---|
| 17 | 0 | 143 | 0 |
| 24 | 0 | 150 | 0 |
| 30 | 0 | 160 | 0 |
| 33 | 0 | 164 | 0 |
| 36 | 0 | 170 | 0 |
| 45 | 0 | 177 | 0 |
| 49 | 0 | 186 | 0 |
| 53 | 0 | 190 | 0 |
| 68 | 0 | 196 | 0 |
| 87 | 0 | 202 | 0 |
| 91 | 0 | 205 | 0 |
| 95 | 0 | 227 | 0 |
| 140 | 0 | 374 | 0 |
| 141 | 0 | | |

What is claimed is:
1. A 3(2H)-pyridazinone of formula (I):

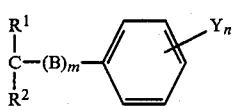

wherein,
A denotes a straight or branched $C_1$ to $C_6$ alkyl, R denotes a straight or branched $C_1$ to $C_6$ alkyl, X denotes oxygen or sulfur atom,
Q denotes a group:

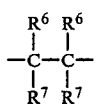

$R^1$ and $R^2$ denote each independently hydrogen, a lower alkyl, a lower haloalkyl, or 4-tert-butylphenyl,
B denotes a —$CR^6$=$CR^7$—, —$CR^6R^7O$— or $$-\underset{R^7}{\overset{R^6}{\underset{|}{C}}}-\underset{R^7}{\overset{R^6}{\underset{|}{C}}}-$$

$R^6$ and $R^7$ denote each independently hydrogen or a $C_1$ to $C_3$ alkyl
m is 0 or 1,
Y denotes hydrogen, a halogen, a $C_1$ or $C_6$ alkyl, a cycloalkyl, a cycloalkyloxy, a $C_1$ to $C_6$ alkyloxy, a $C_1$ to $C_6$ alkylthio, a $C_1$ to $C_6$ alkylsulfinyl, a $C_1$ to $C_6$ alkylsulfonyl, a lower haloalkyl, a lower haloalkyloxy, a lower haloalkylthio, a lower alkenyloxy, trimethylsilyl, a lower alkoxycarbonyl, dimethylamino, nitro, cyano, SCN,

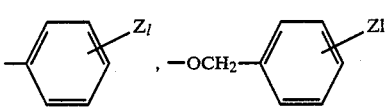

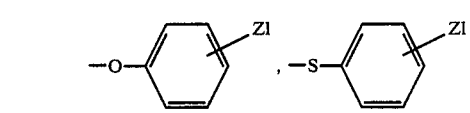

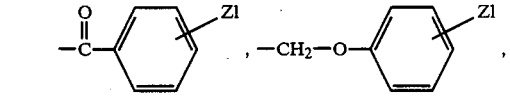

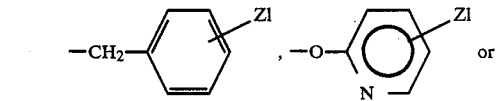

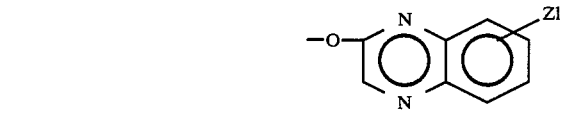

(wherein, Z denotes a halogen, a lower alkyl, a lower alkoxy, a cycloalkyl, a lower haloalkyl, a lower alkoxycarbonyl or nitro and l is 1 or an integer of from 1 to 5, said Z being the same or different when l is an integer of 2 to 5), n is an integer of from 1 to 5, said Y being the same or different when n is an integer of 2 to 5.

2. The compound according to claim 1, wherein R denotes tertbutyl, A denotes methyl, $R^1$ and $R^2$ denote each independently hydrogen or methyl, B denotes $-CR^6=CR^7-$ (wherein, $R^6$ and $R^7$ denote each independently hydrogen or methyl), Y denotes hydrogen, a halogen, a $C_1$ to $C_6$ alkyl, a $C_3$ to $C_6$ cycloalkyl, a $C_3$ to $C_6$ cycloalkyloxy, a $C_1$ to $C_6$ alkyloxy, a $C_1$ to $C_6$ haloalkyl, a $C_1$ to $C_6$ haloalkyloxy, a $C_3$ to $C_6$ alkenyloxy, trimethylsilyl,

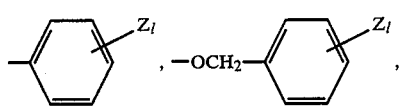

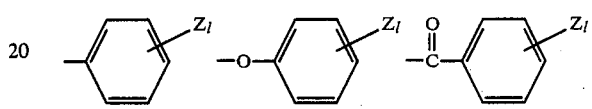

(wherein, Z denotes a halogen, a lower alkyl, a lower alkoxy or a lower haloalkyl and l is 0 or an integer of from 1 to 5, said Z being the same or different when l is an integer of 2 to 5).

3. The compound according to claim 2, wherein R denotes tertbutyl, A denotes methyl, $R^1$ and $R^2$ denote each independently hydrogen or methyl, Y denotes a halogen, a $C_1$ to $C_6$ alkyl, a $C_3$ to $C_6$ cycloalkyl, a $C_3$ to $C_6$ cycloalkyloxy, a $C_1$ to $C_6$ alkyloxy, a $C_1$ to $C_4$ haloalkyl, a $C_1$ to $C_4$ haloalkyloxy, trimethylsilyl, (wherein, Z denotes a halogen or a lower haloalkyl and l is 0 or an integer of from 1 to 2, said Z being the same or different when l is an integer of 2), and X denotes oxygen or sulfur atom, m denotes 0 and n is a integer of 1 to 2, said Y being the same or different when n is 2.

* * * * *